(12) United States Patent
Stein

(10) Patent No.: US 11,771,448 B2
(45) Date of Patent: Oct. 3, 2023

(54) SYSTEM AND METHOD FOR LEAD EXTRACTION

(71) Applicant: Uri Stein, Jerusalem (IL)

(72) Inventor: Uri Stein, Jerusalem (IL)

(73) Assignee: XTRAC O.S LTD., Raanana (IL)

( * ) Notice: Subject to any disclaimer, the term of this patent is extended or adjusted under 35 U.S.C. 154(b) by 514 days.

(21) Appl. No.: 16/769,245

(22) PCT Filed: Dec. 4, 2018

(86) PCT No.: PCT/IL2018/051332
§ 371 (c)(1),
(2) Date: Jun. 3, 2020

(87) PCT Pub. No.: WO2019/111255
PCT Pub. Date: Jun. 13, 2019

(65) Prior Publication Data
US 2021/0186539 A1    Jun. 24, 2021

Related U.S. Application Data

(60) Provisional application No. 62/594,034, filed on Dec. 4, 2017.

(51) Int. Cl.
*A61B 17/22*   (2006.01)
*A61B 17/34*   (2006.01)
*A61N 1/05*    (2006.01)
*A61B 17/00*   (2006.01)
*A61B 90/00*   (2016.01)

(52) U.S. Cl.
CPC .... *A61B 17/22012* (2013.01); *A61B 17/3468* (2013.01); *A61N 1/056* (2013.01); *A61B 2017/00243* (2013.01); *A61B 2090/3966* (2016.02)

(58) Field of Classification Search
CPC .......... A61B 17/22012; A61B 17/3468; A61B 2017/00243; A61N 1/056; A61N 2001/0578
See application file for complete search history.

(56) References Cited

U.S. PATENT DOCUMENTS

| | | | |
|---|---|---|---|
| 4,582,056 A | 4/1986 | McCorkle, Jr. | |
| 6,772,014 B2 * | 8/2004 | Coe | A61N 1/056 606/108 |
| 2003/0036788 A1 | 2/2003 | Coe et al. | |
| 2009/0234367 A1 | 9/2009 | Verma | |
| 2013/0116704 A1 | 5/2013 | Geistert | |
| 2013/0150695 A1 | 6/2013 | Biela et al. | |
| 2015/0367123 A1 | 12/2015 | Kalmann et al. | |
| 2017/0333016 A1 | 11/2017 | Roeder et al. | |

FOREIGN PATENT DOCUMENTS

| | | |
|---|---|---|
| CN | 103635228 A | 3/2014 |
| RU | 2007137214 A | 4/2009 |

\* cited by examiner

*Primary Examiner* — Kelly J Bekker
*Assistant Examiner* — Mohammed S Adam
(74) *Attorney, Agent, or Firm* — ALPHAPATENT ASSOCIATES, LTD; Daniel J. Swirsky

(57) ABSTRACT

A method for extracting a lead from a patient comprising: providing a lead removal stylet; inserting the stylet into the lead; locking the stylet to a position inside the lead; and vibrating the stylet with tissue disrupting vibration to cause the lead to vibrate and to disconnect from binding tissue.

10 Claims, 23 Drawing Sheets

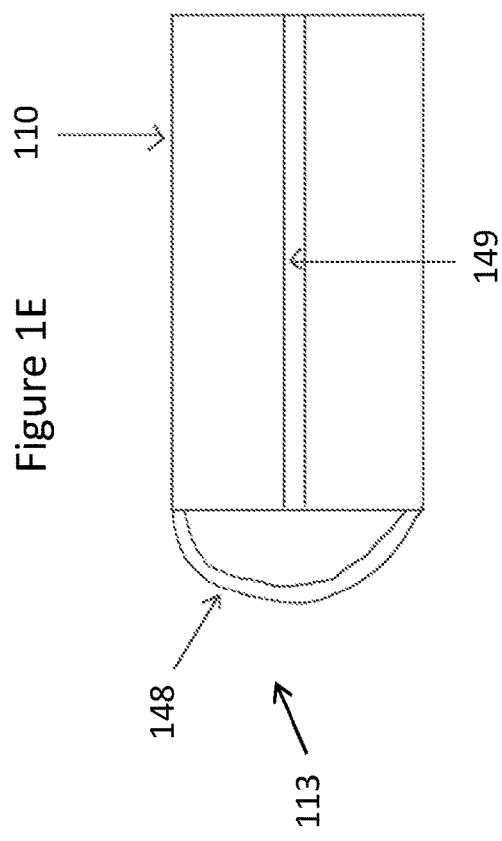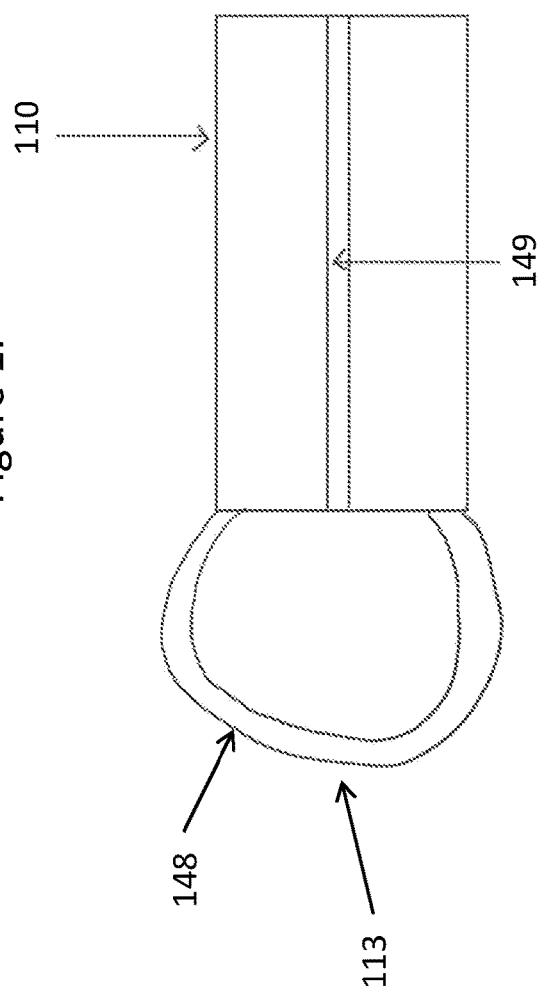

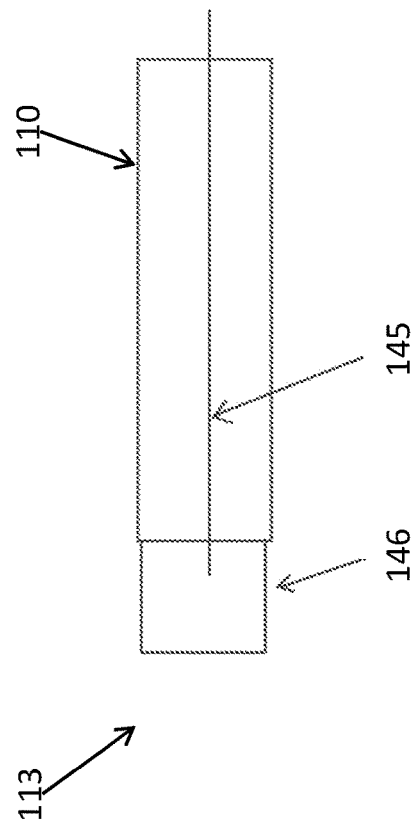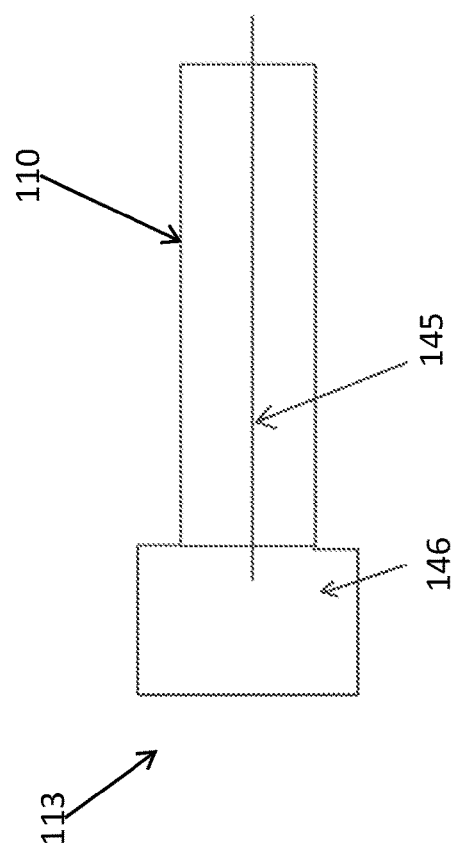

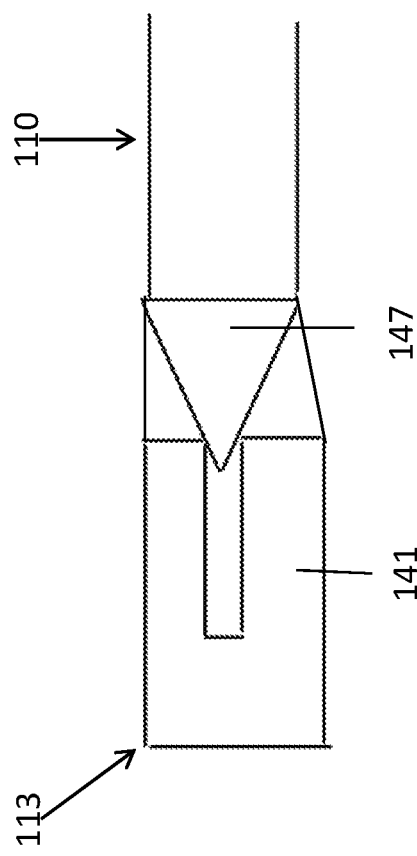
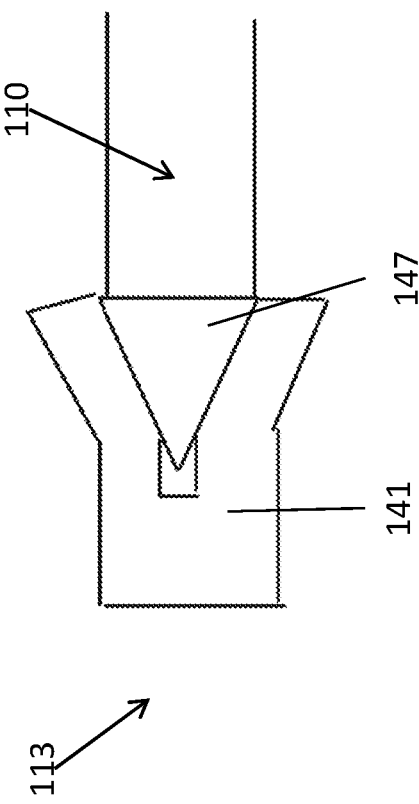

SYSTEM AND METHOD FOR LEAD EXTRACTION

CROSS-REFERENCE TO RELATED APPLICATIONS

This application is a U.S. National Phase Application under 35 U.S.C. 371 of International Application No. PCT/IL2018/051332, which has an international filing date of Dec. 4, 2018, and which claims priority and benefit from U.S. Provisional Patent Application No. 62/594,034, filed Dec. 4, 2017, the contents and disclosure of which are incorporated herein by reference in their entirety.

FIELD OF THE DISCLOSURE

The present disclosure is of a system and method for removing an implanted lead from a patient and in particular, such a system and method that significantly improves the removal process of such a cardiac lead.

BACKGROUND OF THE DISCLOSURE

Pacemaker or ICD (implantable cardioverter-defibrillator) leads are fed into the heart through a large vein and connect the pacemaker to the implantation site of an electrode that terminates the lead which is implanted in the heart. Sometimes these inserted leads need to be removed due to one or more reasons including infection, malfunction, lead degradation, pacing system upgrade, or venous occlusion/stenosis.

Ideally (if the lead has been implanted for a short time) it should be possible to remove the lead by simple traction, however this is typically not the case. Lead removal is usually complicated by the lead's attachments to the patient's body at various places in the pathway from cardiac rhythm device to heart muscle, since the human body tends to incorporate foreign devices into tissue. These tissue growths (binding sites) thus hold the lead and pulling on the lead to remove it may actually endanger the patient by resulting in perforation of the heart or vein wall.

In these cases the most common method of removal uses a cutting device which threads over the lead and is moved along the lead to remove any tissue attachments with a cutting tube, cutting lasers or other cutting methods. These cutting sheath or laser sheath solutions also cause problems since the tissue that is dislodged by the sheath tends to build up in front of the sheath eventually clogging the pathway that the sheath was supposed to clear.

Another option is to leave the existing lead in position and insert a new lead but this is not a preferred solution as the unused lead provides additional obstruction to blood flow and heart valve function and may become infected.

Thus, there is an urgent need for an alternative solution for cardiac lead removal that significantly eases the process of lead removal and reduces the risk to patients.

SUMMARY OF THE DISCLOSURE

The present disclosure overcomes the deficiencies of the background art by providing an improved system and method for cardiac lead removal. The system comprises a lead removal stylet (LRS) that is inserted into the interior of the lead to be removed (hereinafter referred to as the lead). The LRS is moved through the lead's internal lumen and the LRS tip is extensively vibrated at tissue binding sites to dislodge the binding tissue. Alternatively the LRS is vibrated along the entire length of the LRS to simultaneously dislodge binding tissue at all binding sites allowing the lead to then be removed.

In order to detect a binding site the LRS is locked to a position against the inner walls of the lead, a low amplitude testing vibration is applied to the LRS, and the resistance to the vibration is measured. The level of resistance provides an indication as to whether the lead is stuck to local tissue. Where a binding site is detected, higher levels of vibration are applied to dislodge the binding tissue. If no tissue binding is detected then the LRS is moved to a next position in the lead and process is repeated until the lead is completely freed from tissue binding and can be removed.

The process of moving the LRS, checking for resistance, and applying tissue-disrupting vibration is preferably automated and controlled by an LRS controller which is a computing device. Alternatively the process is controlled by a human operator such as a medical professional operating the controller and making decisions about when and where to move the LRS, when to apply vibration, and how much to apply. Alternatively the process is controlled by a human operator with the controller providing automated assistance, for example allowing the controller to select the type and amplitude of vibration to apply.

According to some embodiments of the present disclosure, a method for extracting a lead from a patient comprises: providing a lead removal stylet; inserting the stylet into the lead; locking the stylet to a position inside the lead; and vibrating the stylet with tissue disrupting vibration to cause the lead to vibrate and to disconnect from binding tissue. Optionally the method further comprises vibrating the stylet with testing vibration to determine the resistance to the testing vibration. Preferably when the resistance to the testing vibration is high, applying tissue disrupting vibration. Optionally the method further comprises determining the resistance to testing vibration to determine whether further tissue disruption vibration is required. Optionally the method further comprises removing the lead. Preferably the method further comprises providing a controller for the LRS and wherein the locking the stylet to a position inside the lead, the vibrating the stylet with tissue disrupting vibration, the vibrating the stylet with testing vibration; and the determining the resistance to testing vibration to determine whether further tissue disruption vibration is required are performed by the controller.

According to some further embodiments of the present disclosure, a method for disconnecting a lead from binding tissue comprises: providing a lead removal stylet; inserting the stylet into the lead; locking the stylet to a position inside the lead adjacent to the binding tissue; and vibrating the stylet to cause the lead to vibrate and to disconnect from the binding tissue.

According to some further embodiments of the present disclosure, a system for cardiac lead extraction comprises: a lead removal stylet adapted for insertion into a lead and comprising a locking mechanism for locking the stylet to a portion of the inside wall of the lead; and means for vibrating the stylet. Preferably the system further comprises a controller, wherein the controller controls the movement of the stylet and the type of vibration applied. Optionally the type of vibration comprises vibration selected from the group consisting of: horizontal, rotational, vertical, a combination of directions; high amplitude; low amplitude; long period; short period; high frequency; low frequency; and a combination of the above.

Optionally the locking mechanism is adapted to transfer the vibrations from the stylet to the lead. Optionally the locking mechanism is radiopaque. Optionally the locking mechanism comprises a cable locking head formed of a flexible material manipulated by a locking cable. Optionally the locking mechanism comprises a balloon locking head comprising an inflatable material. Optionally the locking mechanism comprises a heated transform lock comprising a material that deforms when heated. Optionally the material that deforms comprises Nitinol. Optionally the locking mechanism comprises a wedge and dowel. Optionally the stylet is disposable.

According to some further embodiments of the present disclosure, a method for disconnecting a lead from binding tissue comprises: providing a lead removal stylet; inserting the stylet into the lead; locking the stylet inside the lead along the full length of the lead; and vibrating the stylet to cause the lead to vibrate and to disconnect from the binding tissue. Optionally the method further comprises providing a controller for the LRS and wherein the locking the stylet inside the lead, and the vibrating the stylet are performed by the controller.

According to some further embodiments of the present disclosure, a system for cardiac lead extraction comprising: a lead removal stylet adapted for insertion into a lead and comprising a locking mechanism for locking the stylet to a plurality of positions on the inside wall of the lead; and means for vibrating the stylet along its entire length. Preferably the system further comprises a controller, wherein the controller controls the movement of the stylet and the type of vibration applied. Preferably the locking mechanism transfers the vibrations from the stylet to the lead. Optionally the locking mechanism is radiopaque.

Optionally the locking mechanism comprises a plurality of cable locking heads each formed of a flexible material manipulated by a locking cable. Optionally the locking mechanism comprises a plurality of balloon locking heads comprising an inflatable material. Optionally the locking mechanism comprises a plurality of heated transform locks comprising a material that deforms when heated. Optionally the material that deforms comprises Nitinol. Optionally the locking mechanism comprises multiple wedge and dowel locks Lead as used herein refers to a cardiac lead or cardiac catheter. Alternatively lead may also refer to other types of leads or catheters that are implanted in a patient and that require removal. As used herein distal refers to those parts of the lead or LRS that are furthest from the LRS controller and proximal refers to parts that are closest to the LRS controller.

Unless otherwise defined, all technical and scientific terms used herein have the same meaning as commonly understood by one of ordinary skill in the art to which this disclosure belongs. The materials, methods, and examples provided herein are illustrative only and not intended to be limiting.

Implementation of the method and system of the present disclosure involves performing or completing certain selected tasks or steps manually, automatically, or a combination thereof. Moreover, according to actual instrumentation and equipment of preferred embodiments of the method and system of the present disclosure, several selected steps could be implemented by hardware or by software on any operating system of any firmware or a combination thereof. For example, as hardware, selected steps of the disclosure could be implemented as a chip or a circuit. As software, selected steps of the disclosure could be implemented as a plurality of software instructions being executed by a computer using any suitable operating system. In any case, selected steps of the method and system of the disclosure could be described as being performed by a data processor, such as a computing platform for executing a plurality of instructions.

Although the present disclosure is described with regard to a "computing device", a "computer", or "device", or "mobile device" on a "computer network" or simply "network", it should be noted that optionally any device featuring a data processor and the ability to execute one or more instructions may be described as a computer or one of the interchangeable terms listed above, including but not limited to any type of personal computer (PC), a server, a cellular telephone, an IP telephone, a smartphone, or a PDA (personal digital assistant). Any two or more of such devices in communication with each other may optionally comprise a "network".

BRIEF DESCRIPTION OF THE DRAWINGS

The disclosure will now be described in connection with certain preferred embodiments with reference to the following illustrative figures so that it may be more fully understood. With specific reference now to the figures in detail, it is stressed that the particulars shown are by way of example and for purposes of illustrative discussion of the preferred embodiments of the present disclosure only and are presented in the cause of providing what is believed to be the most useful and readily understood description of the principles and conceptual aspects of the disclosure. In this regard, no attempt is made to show structural details of the disclosure in more detail than is necessary for a fundamental understanding of the disclosure, the description taken with the drawings making apparent to those skilled in the art how the several forms of the disclosure may be embodied in practice.

In the drawings:

FIGS. 1A-1M are schematic system diagrams showing a system for lead removal according to some embodiments of the present disclosure;

DETAILED DESCRIPTION OF PREFERRED EMBODIMENTS

Figure 1A:
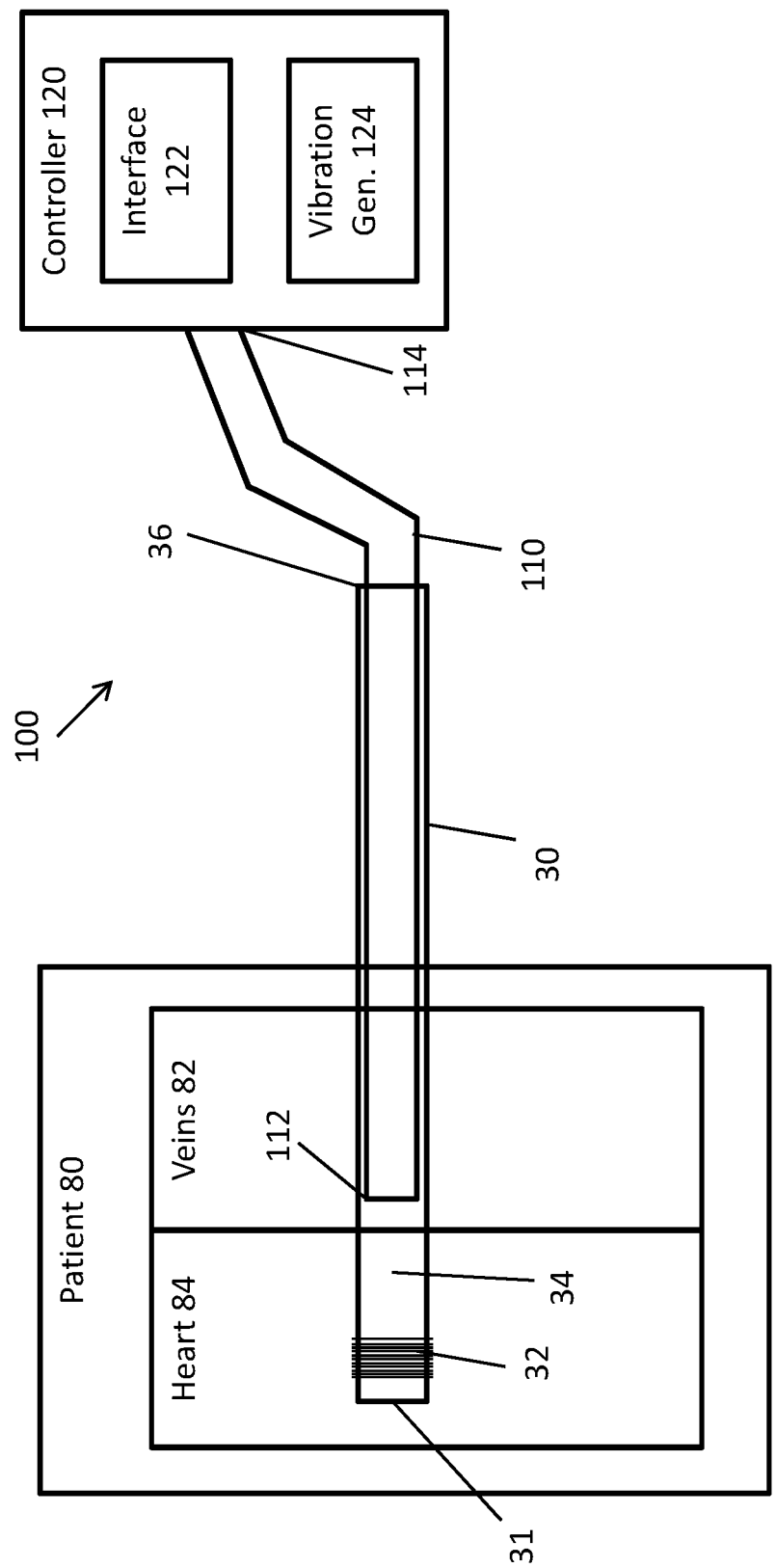

In the detailed description, numerous specific details are set forth in order to provide a thorough understanding of the disclosure. However, it will be understood by those skilled in the art that these are specific embodiments and that the present disclosure may be practiced also in different ways that embody the characterizing features of the disclosure as described and claimed herein. In the drawings and descriptions set forth, identical reference numerals indicate those components that are common to different embodiments or configurations.

The present disclosure will be more fully understood from the following detailed description of the preferred embodiments thereof, taken together with the drawings.

Figure 1B:
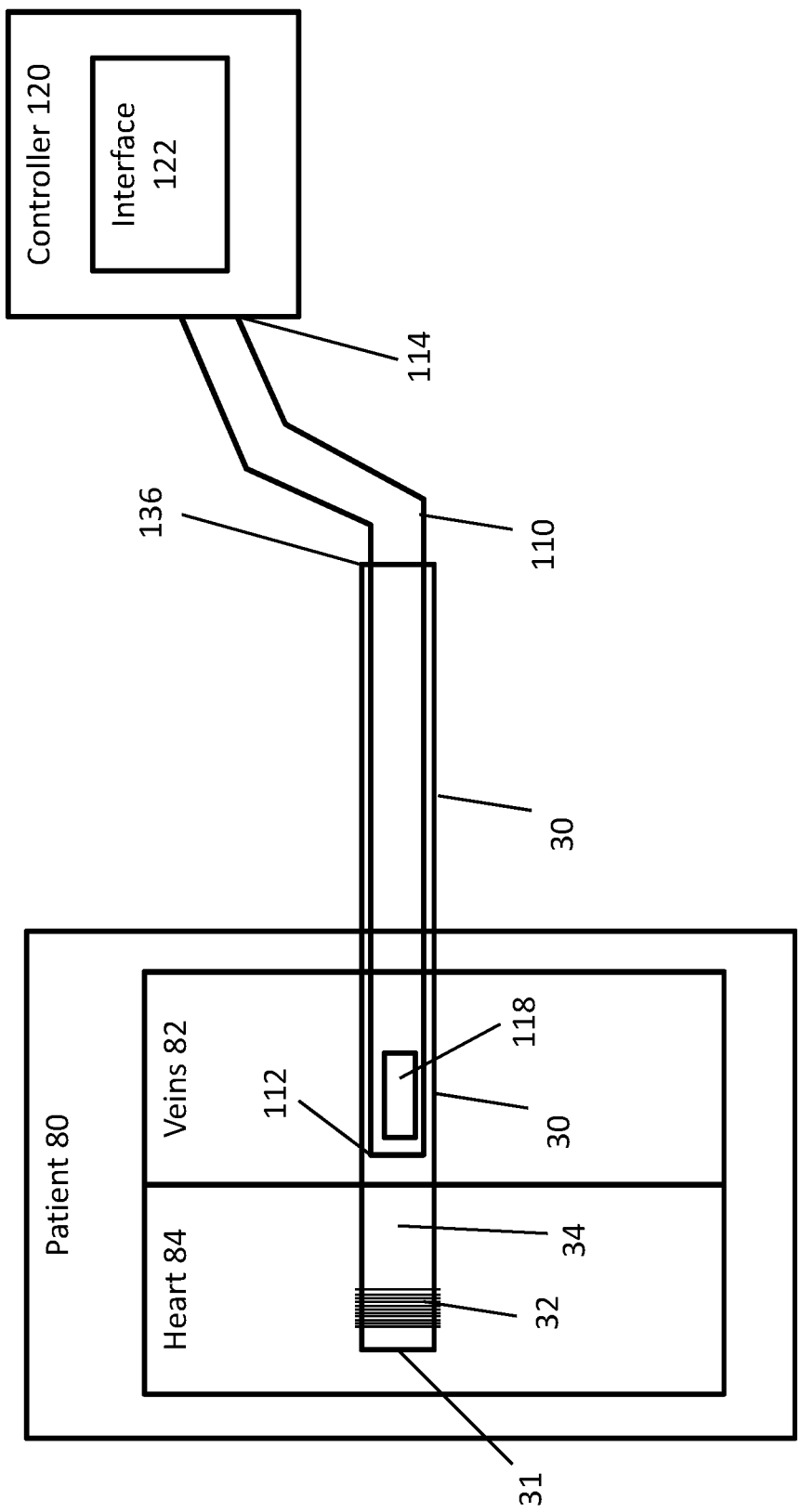

Reference is now made to FIGS. 1A-1D which are schematic system diagrams showing a system for lead removal according to some embodiments of the present disclosure. As shown in FIGS. 1A and 1B, a cardiac lead 30 has been implanted into a patient 80. Lead 30 passes through veins 82 and terminates at its distal end 31 in an electrode 32 that is attached to the heart 84 of patient 80. Lead 30 has an opening 36 at its proximal end that allows access to the interior 34 of lead 30. For the purpose of lead removal it is assumed that lead 30 is disconnected from its source device (such as a pacing device which is not shown).

System 100 for lead removal comprises lead removal stylet (LRS) 110 which is a stylet adapted to fit into lead interior 34 via opening 36. LRS 110 is preferably between 50-100 cm long. LRS 110 comprises a biocompatible material including but not limited to plastic, steel, titanium, or nitinol.

System 100 further comprises controller 120. LRS 110 is attached at its proximal end 114 to controller 120. Controller 120 is a computing device and preferably comprises a controller user interface 122 which comprises interface components as known in the art such as but not limited to a screen, keyboard, mouse or other components for use by an operator (not shown) such as a medical professional to control LRS 110 and to receive information about its activities or status.

Controller 120 also comprises vibration generator 124 which generates the vibrations used by LRS 110 which is attached thereto. Alternatively as shown in FIG. 1B, LRS 110 comprises a vibration generator 118 which can be powered and controlled by controller 120. Optionally system 100 comprises both of generators 124 and 118. Generators 124 and/or 118 are capable of generating a range of vibration frequencies, amplitudes, and directions. Generators 124 and 118 are based on vibration generation mechanisms known in the art including electromagnetically induced vibration or vibration based on piezoelectric transducers. A non limiting example of a vibration generator 124 or 118 is shown in FIG. 1M where vibration generator 124 or 118 comprises a disc 126 attached to motor 127. A vibration cord 129 is attached to disc 126 at attachment point 128. As disc 126 is rotated in direction "A" by motor 127, vibration cord 129 is alternately pushed and pulled in direction "B". Vibration cord 129 is attached to LRS 110 and the mechanical movement "B" translates into a mechanical vibration of LRS 110. Optionally vibration cord 129 is rigid. Optionally vibration cord 129 is rigid in a single plane.

FIGS. 1C-1N show alternative embodiments of locking mechanism 113 used by LRS 110 to lock LRS 110 onto the inner wall 39 of lead 30. The embodiments shown should not be considered limiting and potentially any suitable locking mechanism could be used. Locking mechanism 113 is preferably radiopaque. Locking mechanism 113 is adapted to transfer the vibrations, as described further below, of LRS 110 to lead 30 when locked to lead 30. Locking mechanism 113 is preferably of the same or smaller diameter as outer wall 116 of LRS 110 when in "unlocked" mode allowing LRS 110 to pass through lead 30. Locking mechanism 113 is preferably of a greater diameter than outer wall 116 of LRS 110 when in "locked" mode, pressing locking mechanism 113 against the inside wall 39 of lead 30 to lock LRS 110 to lead 30. Locking mechanism 113 can then be unlocked so that LRS 110 can be removed from lead 30 or moved to another position in lead 30.

Figure 1C:
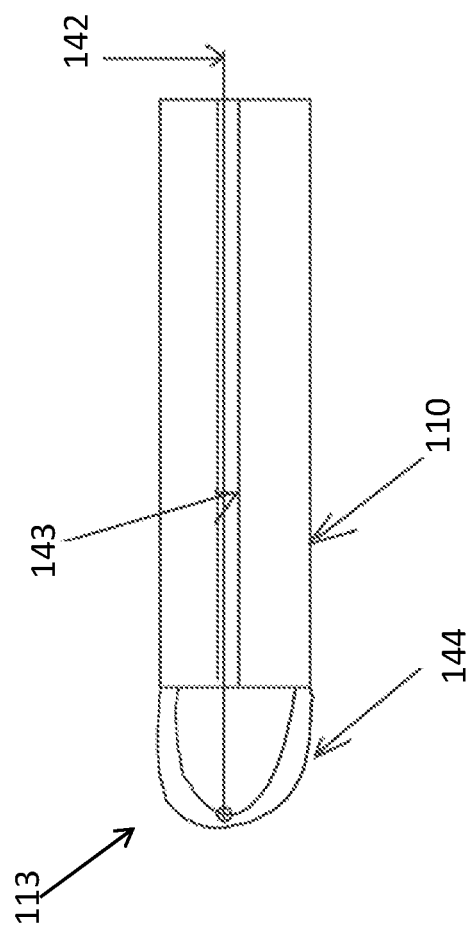
Figure 1D:
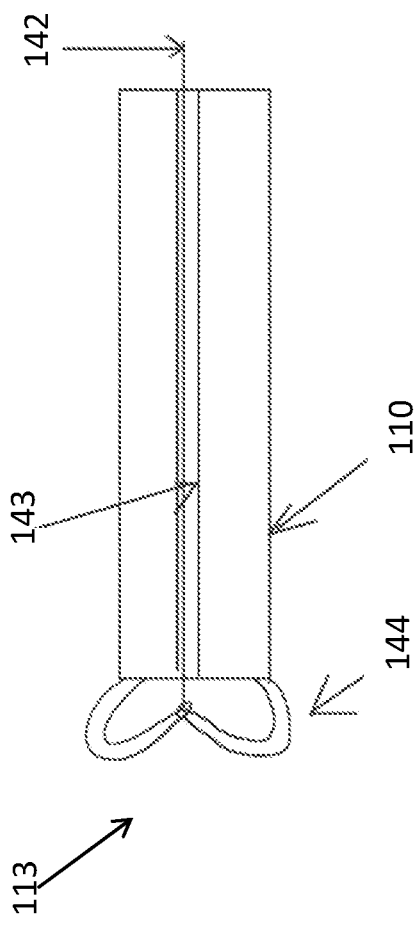

In the embodiment of FIGS. 1C and 1D LRS 110 locking mechanism 113 comprises a cable locking head 144 formed of a flexible material. Locking head 144 is fixedly attached to locking cable 142 which extends from locking head 144 along cable lumen 143. Locking cable 142 exits LRS 110 on its proximal side and can optionally be manipulated by a medical practitioner to lock or unlock LRS 110 to lead 30 or alternatively can be manipulated by controller 120 to lock or unlock LRS 110 to lead 30. FIG. 1C shows locking mechanism 113 in an unlocked position and FIG. 1D shows locking mechanism in a locked position when locking cable 142 is pulled. When locking cable 142 is released, locking head 144 springs back to its original position to unlock from inner wall 39.

In the embodiment of FIGS. 1E and 1F LRS 110 locking mechanism 113 comprises a balloon locking head 148 formed of an inflatable material. Locking head 148 is inflated via inflating lumen 149. Inflating lumen 149 is connected on the proximal side of LRS 110 to an inflating device (not shown) and can optionally be manipulated by a medical practitioner to lock or unlock LRS 110 to lead 30 or alternatively can be manipulated by controller 120 to lock or unlock LRS 110 to lead 30. FIG. 1E shows locking mechanism 113 in an unlocked position and FIG. 1F shows locking mechanism in a locked position when balloon 148 is inflated by a pressurized gas pumped into inflating lumen 149. When the gas is allowed to escape from balloon 148, balloon 148 deflates to unlock from inner wall 39.

Figure 1G:
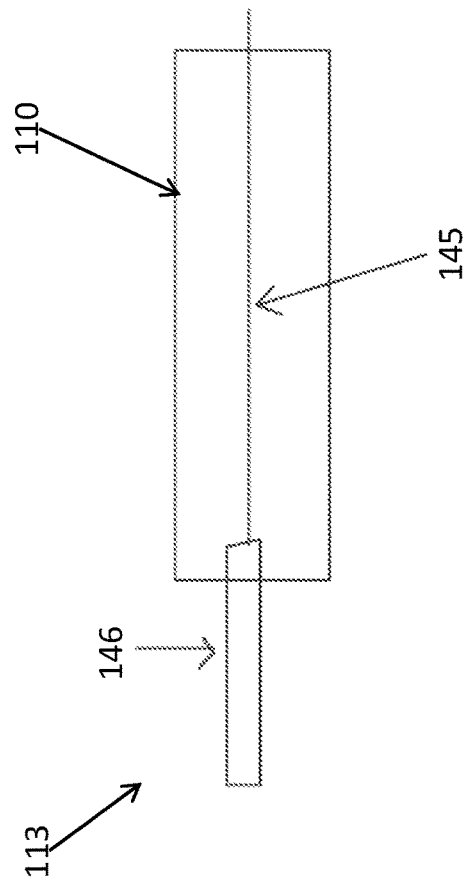
Figure 1H:
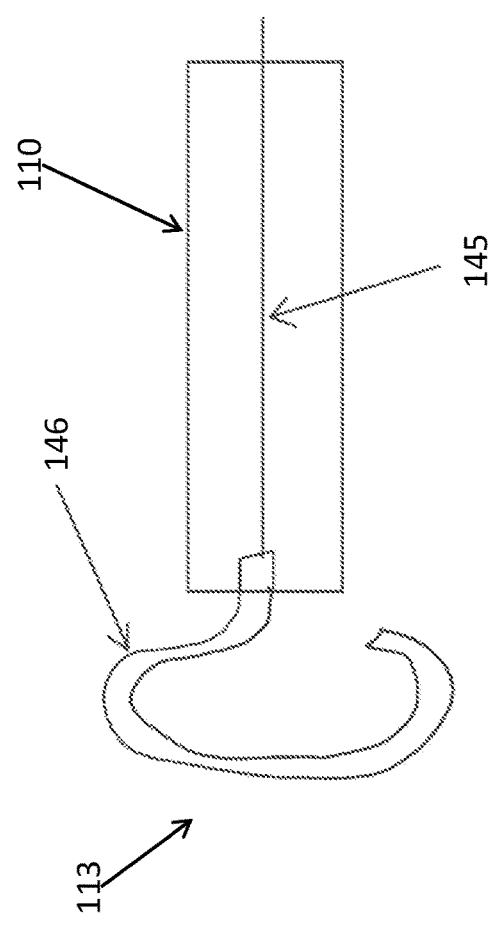
Figure 1M:
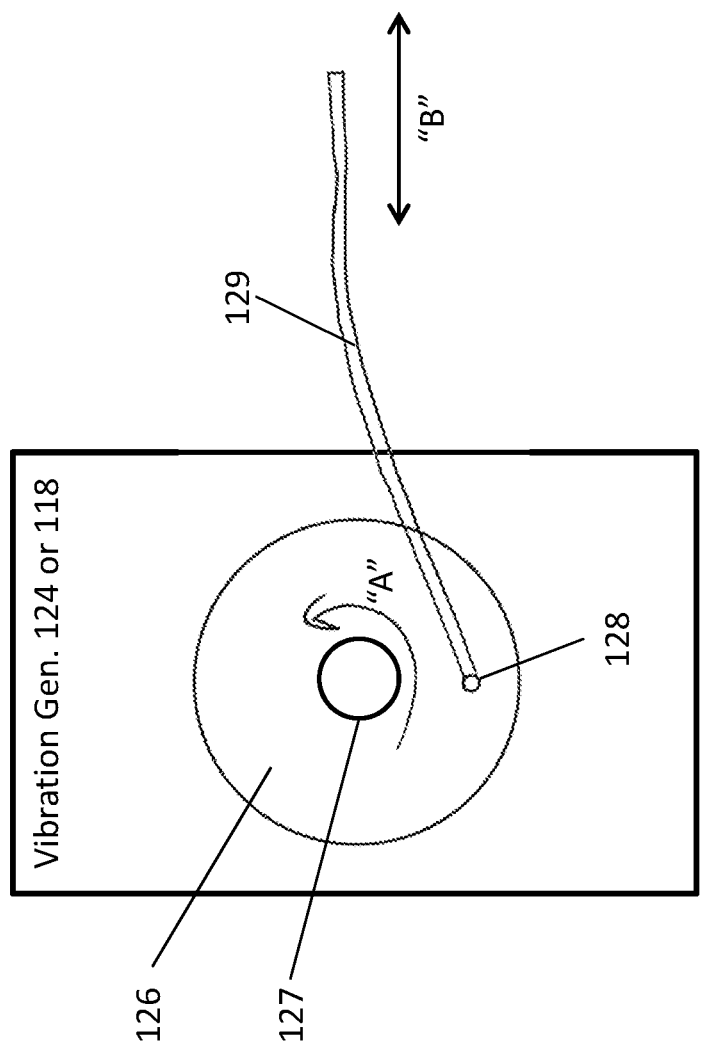

In the embodiment of FIGS. 1G-1J LRS 110 locking mechanism 113 comprises a heated transform lock 146 formed of a material that deforms when heated such as but not limited to Nitinol. Transform lock 146 is fixedly attached to heating wire 145 which extends from transform lock head 146 and exits LRS on its proximal side. Heating wire is heated to thereby heat transform lock 146 and to change the shape of lock 146 to press it against the inner wall 39 of lead 30 to lock LRS 110 at a chosen position. Heating wire 145 is connected at its proximal end to a heating mechanism (not shown) which can optionally be manipulated by a medical practitioner to lock or unlock LRS 110 to lead 30 or alternatively can be manipulated by controller 120 to lock or unlock LRS 110 to lead 30. When heat is removed, lock 146 reverts to its original shape to unlock from inner wall 39. FIGS. 1G and 1I show locking mechanism 113 in an unlocked position and FIGS. 1H and 1J show locking mechanism in a locked position. FIGS. 1G and 1H show a transform lock 146 that curves when heated, and FIGS. 1I and 1J show a transform lock 146 that is cube shaped and expands when heated.

In the embodiment of FIGS. 1K-1L LRS 110 locking mechanism 113 comprises a wedge 147 and dowel 141. In order to lock head 113 to lead 30, dowel 141 is pulled onto wedge 147 or alternatively wedge 147 is driven into dowel 141 such as by rotating LRS 110. When wedge 147 is driven into dowel 141, dowel 141 is opened (FIG. 1L) so as to press against the inner wall 39 of lead 30 to lock LRS 110 at a chosen position. Wedge 147 can optionally be manipulated by a medical practitioner to lock or unlock LRS 110 to lead 30 or alternatively can be manipulated by controller 120 to lock or unlock LRS 110 to lead 30. FIG. 1K shows dowel 141 in an unlocked mode.

Optionally LRS 110 is disposable such that it is used once for each patient. For a disposable LRS 110, LRS 110 connects to controller 120 via interface 114 using a one-use connector (not shown). The one-use connector comprises a mechanism for one-time attachment of LRS 110 to controller 120, such that the connector is damaged after removal from controller 120 preventing reuse.

In use, LRS 110 is inserted into lead interior 34 through opening 36 and then used to detach lead from binding tissue as will be described below.

Figure 2A:
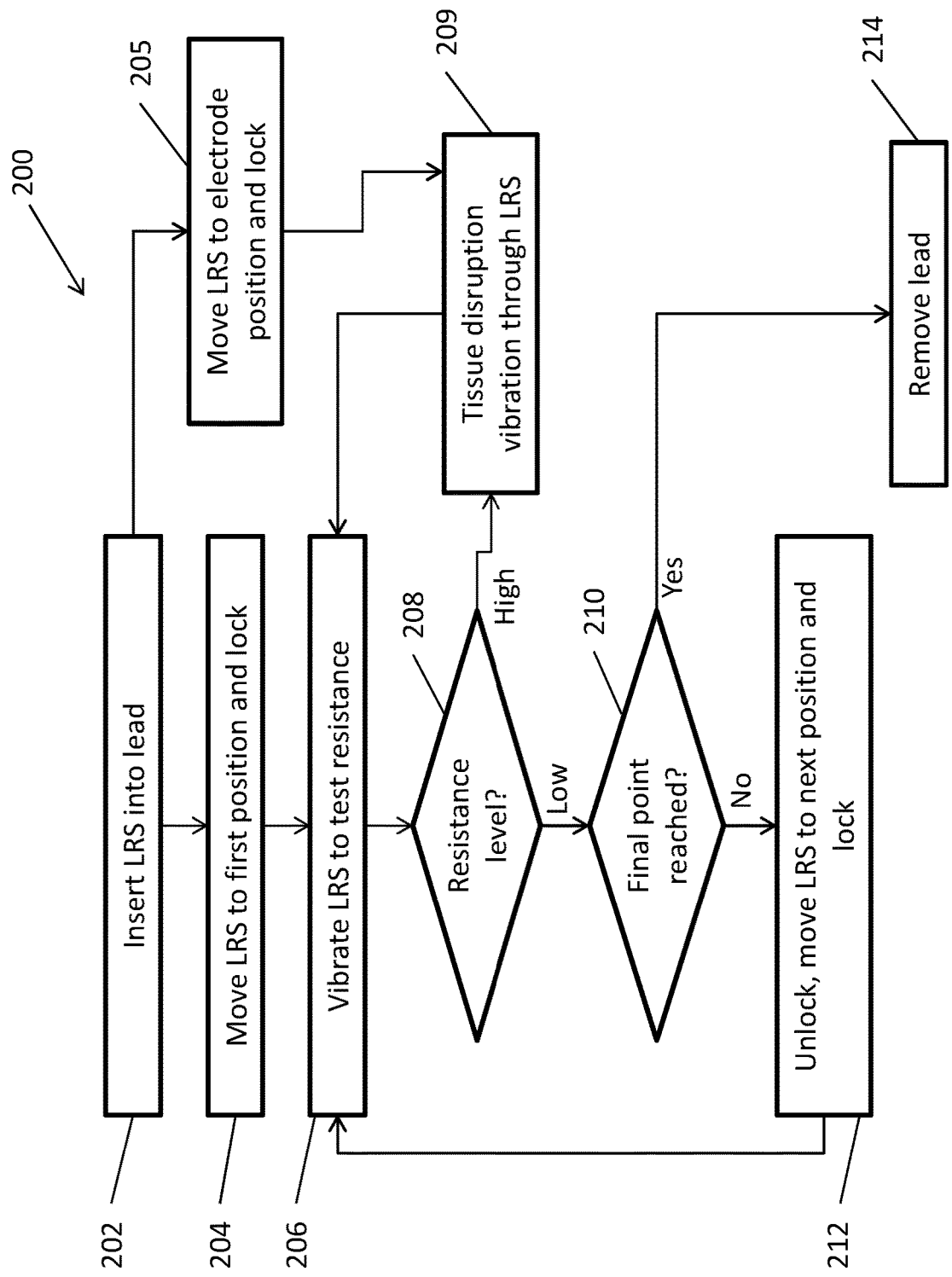
FIGS. 2A and 2B-2H are respectively a flow diagram and illustrative drawings showing a method of use of a lead removal stylet according to at least some embodiments of the present disclosure.
Figure 2B:
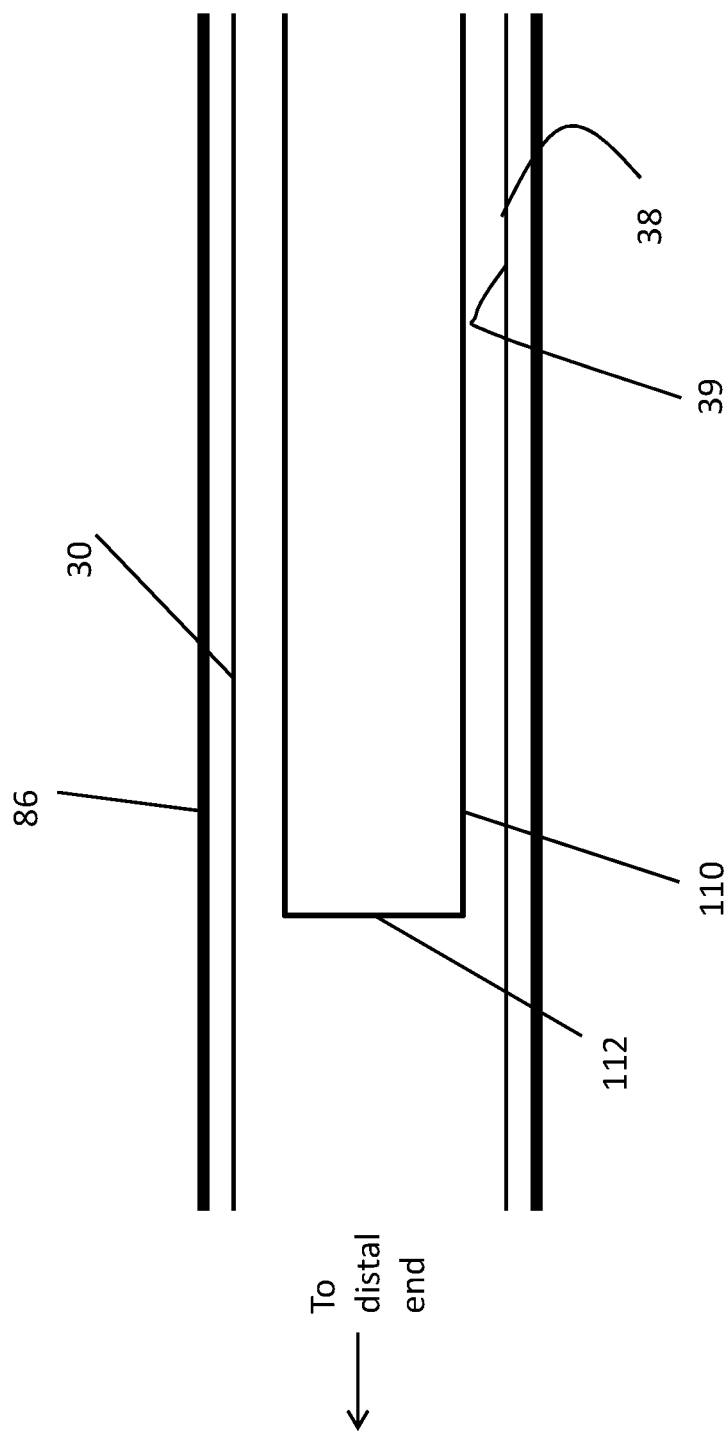

Reference is now made to FIGS. 2A and 2B-2H which are respectively a flow diagram and illustrative drawings showing a method of use of a lead removal stylet according to at least some embodiments of the present disclosure. In step 202 of process 200 as shown in FIG. 2B LRS 110 is inserted into the interior of lead 30. Steps 202-212 are preferably automated and performed by controller 120 or alternatively by controller 120 along with a human operator.

Figure 2C:
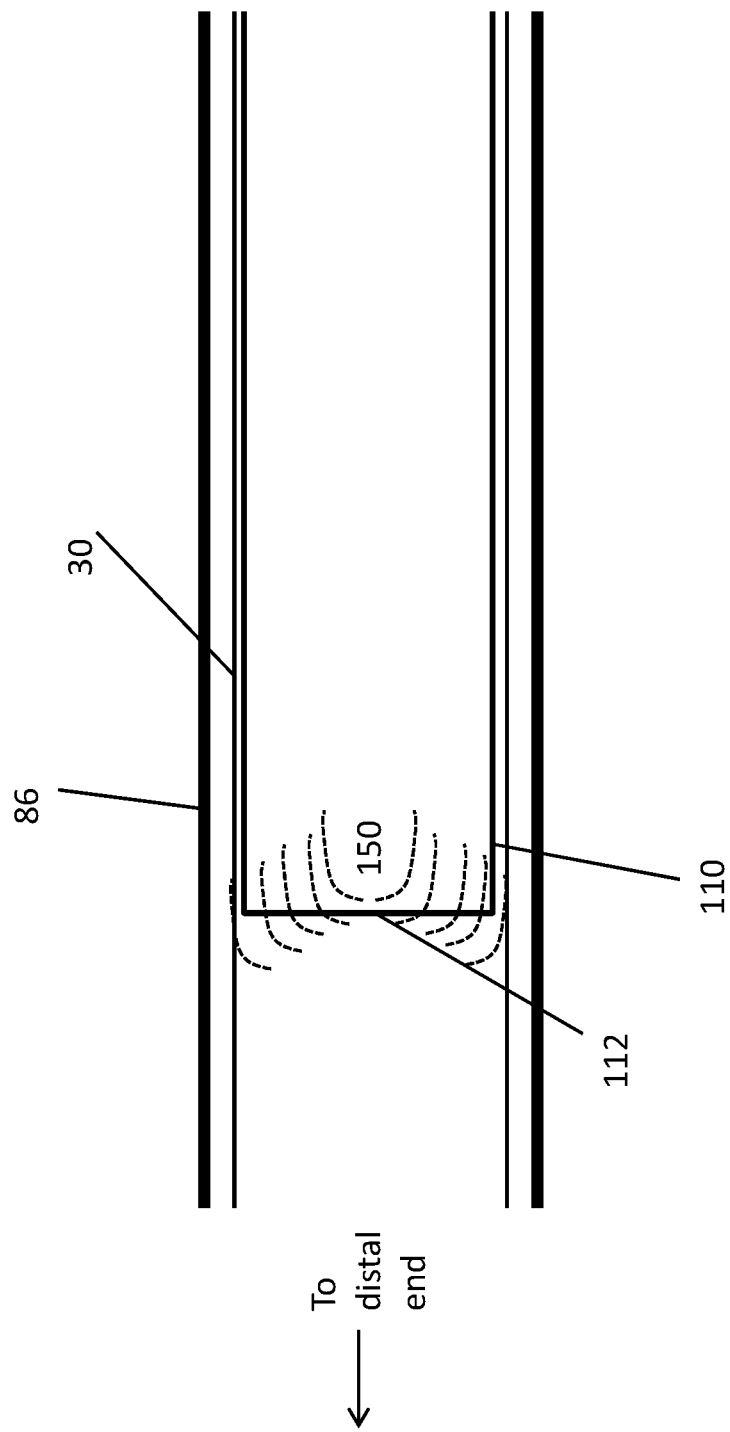
Figure 2D:
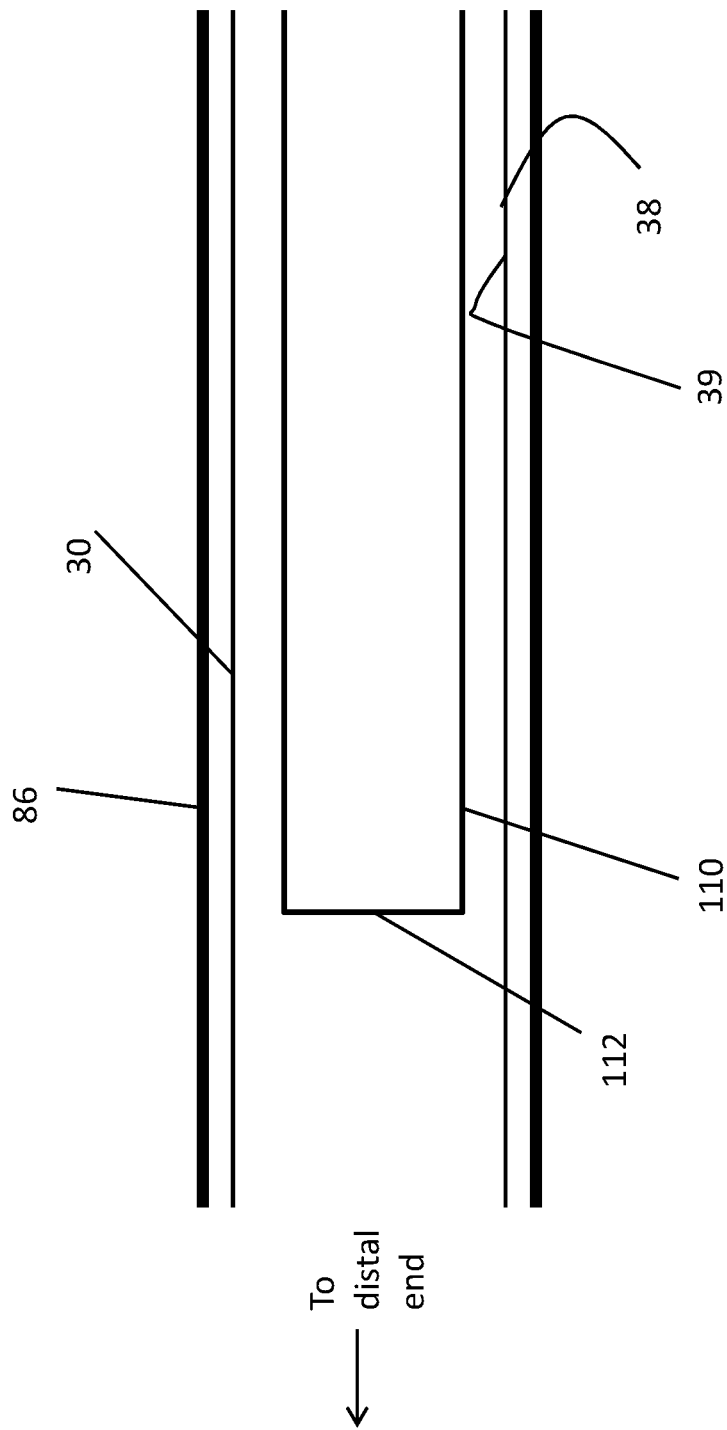

In step 204 and as in FIG. 2B, LRS 110 is moved to a starting position inside lead 30 and as in FIG. 2C; LRS 110 is locked against the inner walls 39 of lead 30 by expanding locking mechanism 113. This position is referred to herein as the locking position. The first locking position is preferably where distal end 112 of LRS 110 is adjacent to electrode 32 as in step 205 and as described further below.

It must now be determined whether lead 30 is held in place by binding tissue 88 or not. Therefore in step 206 and as shown in FIG. 2C, low amplitude testing vibration 150 is activated in or applied to LRS by controller 120 and the resistance to the vibration is measured by controller 120 in step 208. Depending on the measured resistance it is determined whether lead 30 is held in place by binding tissue 88 at the locking position. Test vibration 150 direction is horizontal, rotational, or vertical, or a combination of these in any or all planes. Vibration 150 direction, amplitude, period and frequency (collectively referred to as vibration type) are preferably predetermined based on experience with use of the system on a range of patients. Vibration 150 from LRS 110 is mechanically transferred to lead 30 at the locking position and thus lead 30 also vibrates based on the selected vibration type but to varying degrees depending on the presence of binding tissue 88.

A low resistance to vibration indicates that lead 30 is not stuck in binding tissue 88 at the locking position. Therefore in step 212 and as in FIG. 2D, LRS 110 is unlocked and insertion of LRS 110 continues until the next locking position.

Figure 2E:
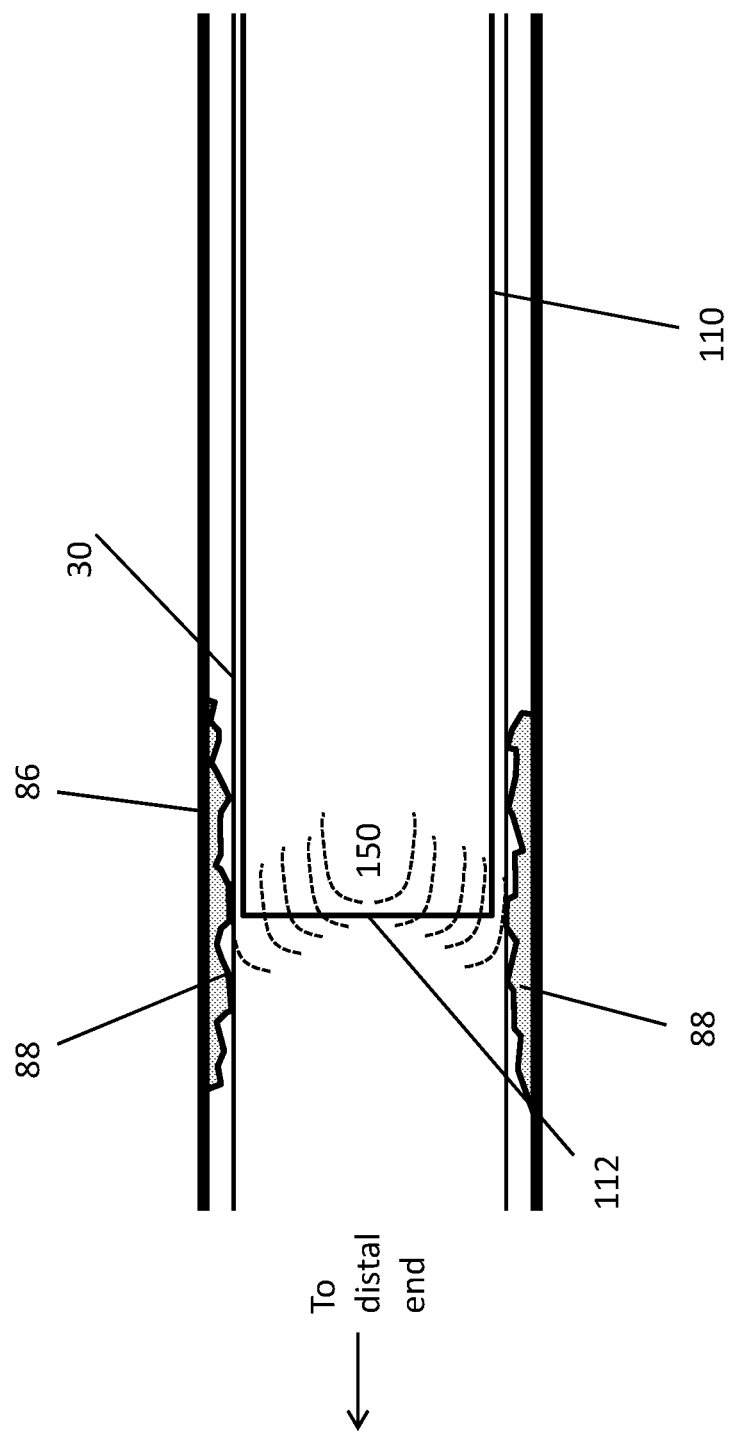
Figure 2F:
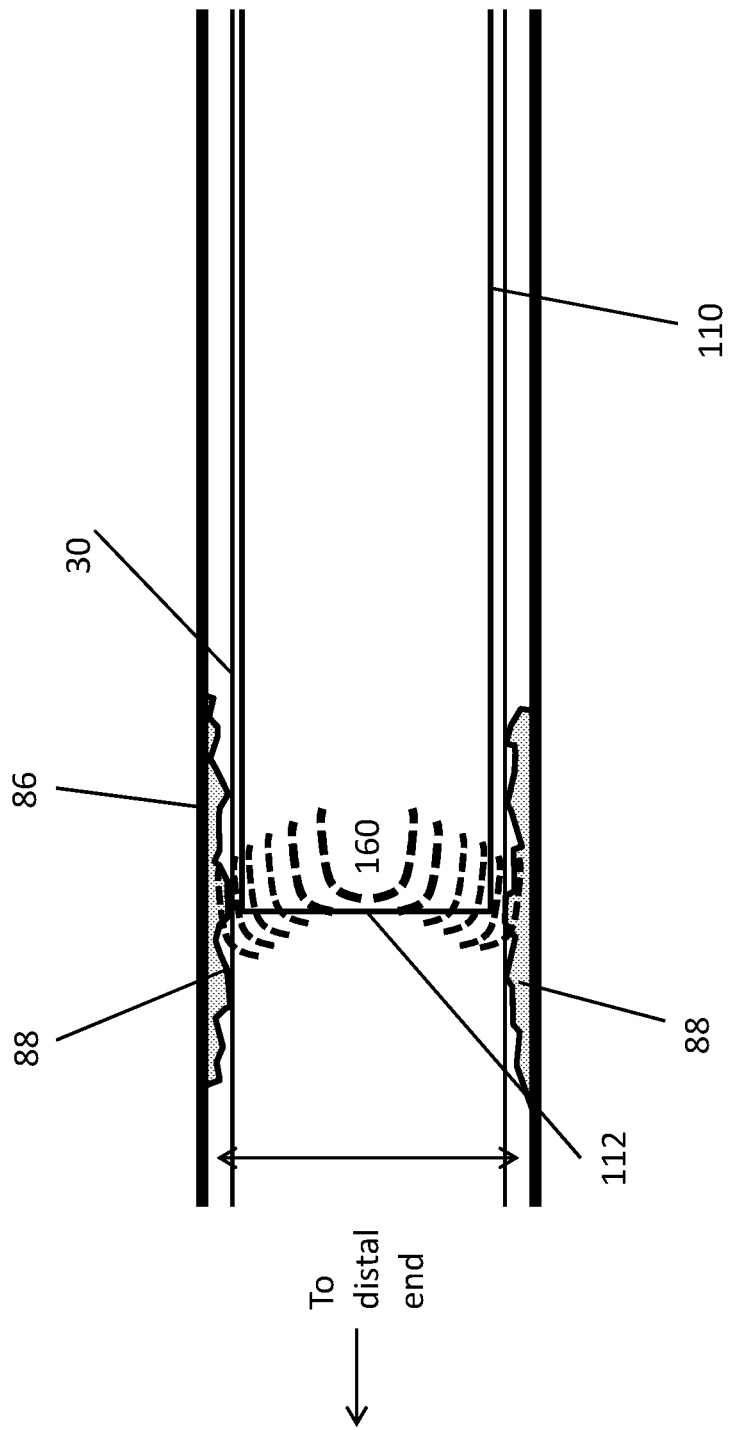
Figure 2G:
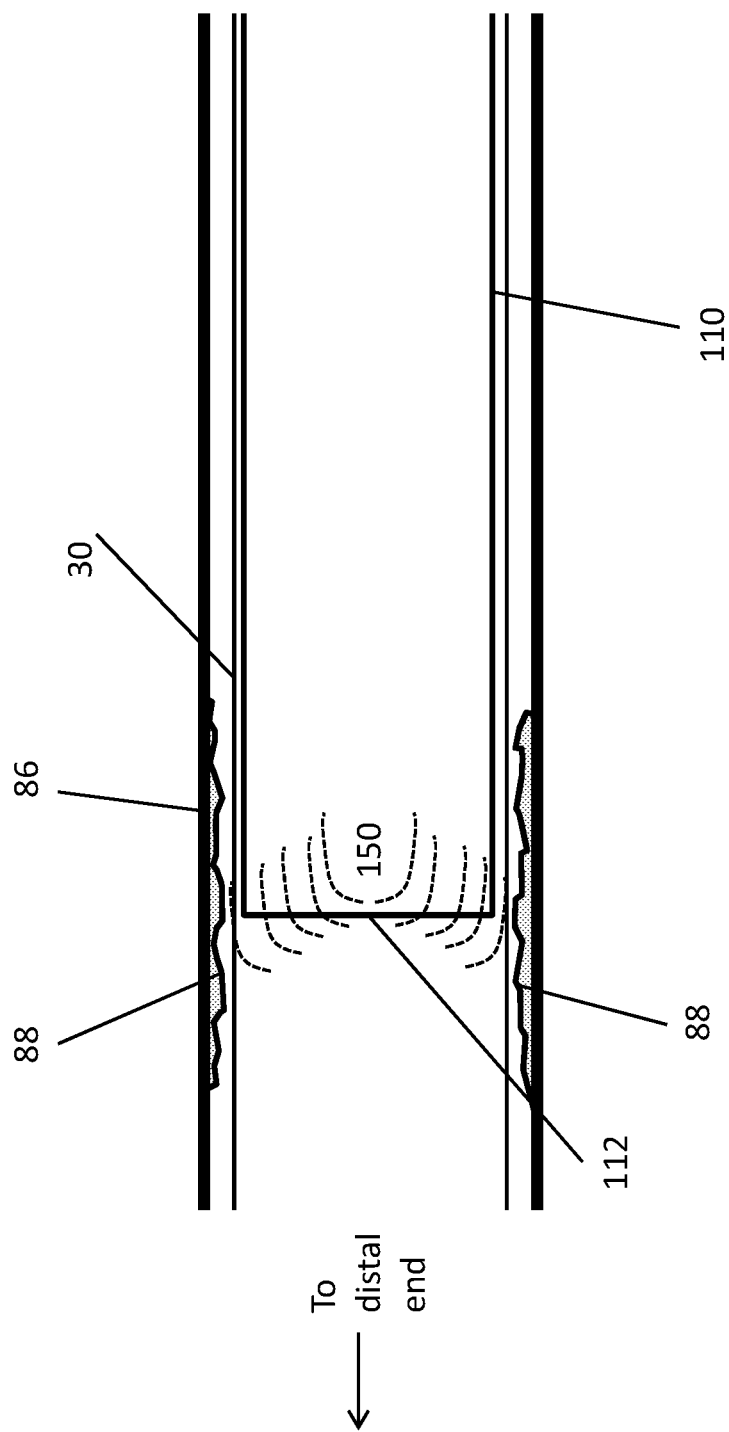

Tissue binding typically occurs where lead 30 exposes a metallic surface to tissue. In these areas, which are visible on an x-ray showing lead 30, locking positions may be 2-10 mm apart. In other parts of lead 30, locking positions may be 10 mm or more apart. Once LRS 110 is locked to the next position, the process for checking resistance as in steps 206 and 208 is repeated (FIGS. 2C, 2E, 2G).

A high resistance to vibration in steps 206 and 208 indicates that lead 30 is stuck in binding tissue 88. FIG. 2E illustrates a locking position where lead 30 is held in position by binding tissue 88. Therefore if the resistance is high, LRS 110 is vibrated with a high amplitude tissue disrupting vibration 160 as at step 209 and as shown in FIG. 2F. As described above, the vibration may be from internal generator 118 or controller generator 124 as in FIGS. 1A and 1B. Tissue disrupting vibration 160 direction is horizontal, or vertical, or a combination of these. Vibration 160 direction, amplitude, period and frequency (collectively referred to as vibration type) are modified depending on the measured level of resistance. Vibration 160 type is preferably predetermined based on experience with use of the system on a range of patients. Vibration 160 from LRS 110 is mechanically transferred to lead 30 at the locking position and thus lead 30 also vibrates based on the selected vibration type. Vibration 160 ideally disrupts binding tissue 88 such as in FIG. 2G.

After completion of the tissue disrupting vibration 160 period, steps 206 and 208 is repeated to determine whether there is still high resistance to testing vibration 150 from LRS 110, in order to assess whether binding tissue 88 has been disrupted. If resistance remains high then step 209 is repeated and high amplitude tissue disrupting vibration 160 is again applied at the locking position. Subsequent applied tissue disrupting vibration 160 is typically of a greater type with increase in one or more of period, frequency or amplitude and also optionally a different vibration direction.

Figure 2H:
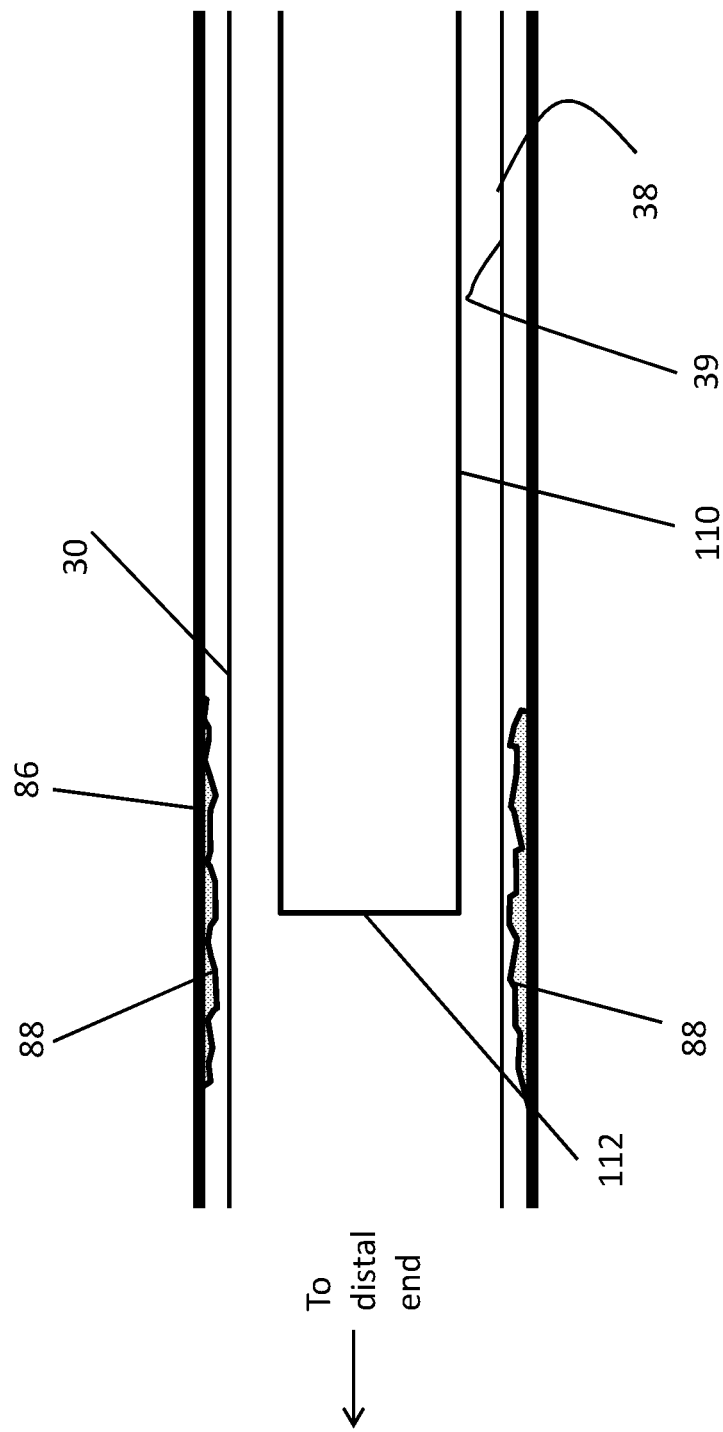

Following the vibration period, LRS 110 is again tested for resistance at the locking position as in steps 206 and 208. Once it has been determined that resistance is lowered it is assumed that binding tissue 88 has been disrupted and that lead 30 is now disconnected from binding tissue 88. Therefore in step 212 and as shown in FIG. 2H, LRS 110 is now unlocked and moved to the next locking position.

The starting position for LRS 110 is preferably where locking mechanism 113 at distal end 112 of LRS 110 is positioned at lead distal end 31 where electrode 32 is located such as in step 205. In such a case, it is known that electrode 32 must be removed from its attachment point in the heart 84 wall. Therefore LRS 110 is locked at the electrode 32 position and as in step 209, LRS 110 is vibrated. As above, the vibration type 160 is adjusted by controller 120 or operator of controller 120. The tissue disrupting vibration 160 of LRS 110 results in transmitted vibration to lead 30 at the locked electrode point. This vibration ideally results in electrode 32 detaching from attached tissue—in this case the heart 84 wall.

To confirm whether the electrode 32 has indeed been loosened, the resistance of LRS 110 at the electrode locking point is measured as in steps 206 and 208. A high resistance indicates that electrode 32 is still attached and step 209 is repeated and tissue disrupting vibration 160 is again applied at the locking position. Subsequent applied tissue disrupting vibration 160 is typically of a greater type with increase in one or more of period, frequency or amplitude and also optionally a different vibration direction. Following the vibration period, LRS 110 is again tested for resistance at the locking position as in steps 206 and 208. Once it has been determined that resistance is lowered it is assumed that electrode 32 has been dislodged. Therefore in step 212 LRS 110 is unlocked and moved to the next locking position.

Following the resistance measurement of steps 206 and 208 and determination that resistance is low, controller 120 or operator assess whether the final locking position has been reached in step 210. If this is the case then in step 214 lead 30 is removed by pulling it out of patient 80.

It should be appreciated from the above that LRS 110 is moved from locking position to locking position in a direction starting from proximal opening 36 of lead 30 and progressing till the distal end 31 of lead 30. Alternatively and preferably, the first locking position of LRS 110 is the distal end 31 of lead 30 (to release electrode 32) followed by locking positions that are progressively closer to proximal opening 36 of lead 30. Alternatively, the first locking position of LRS 110 is the distal end 31 of lead 30 (to release electrode 32) followed by LRS 110 being moved from locking position to locking position in a direction starting from proximal opening 36 of lead 30 and progressing till the distal end 31 of lead 30.

Figure 3A:
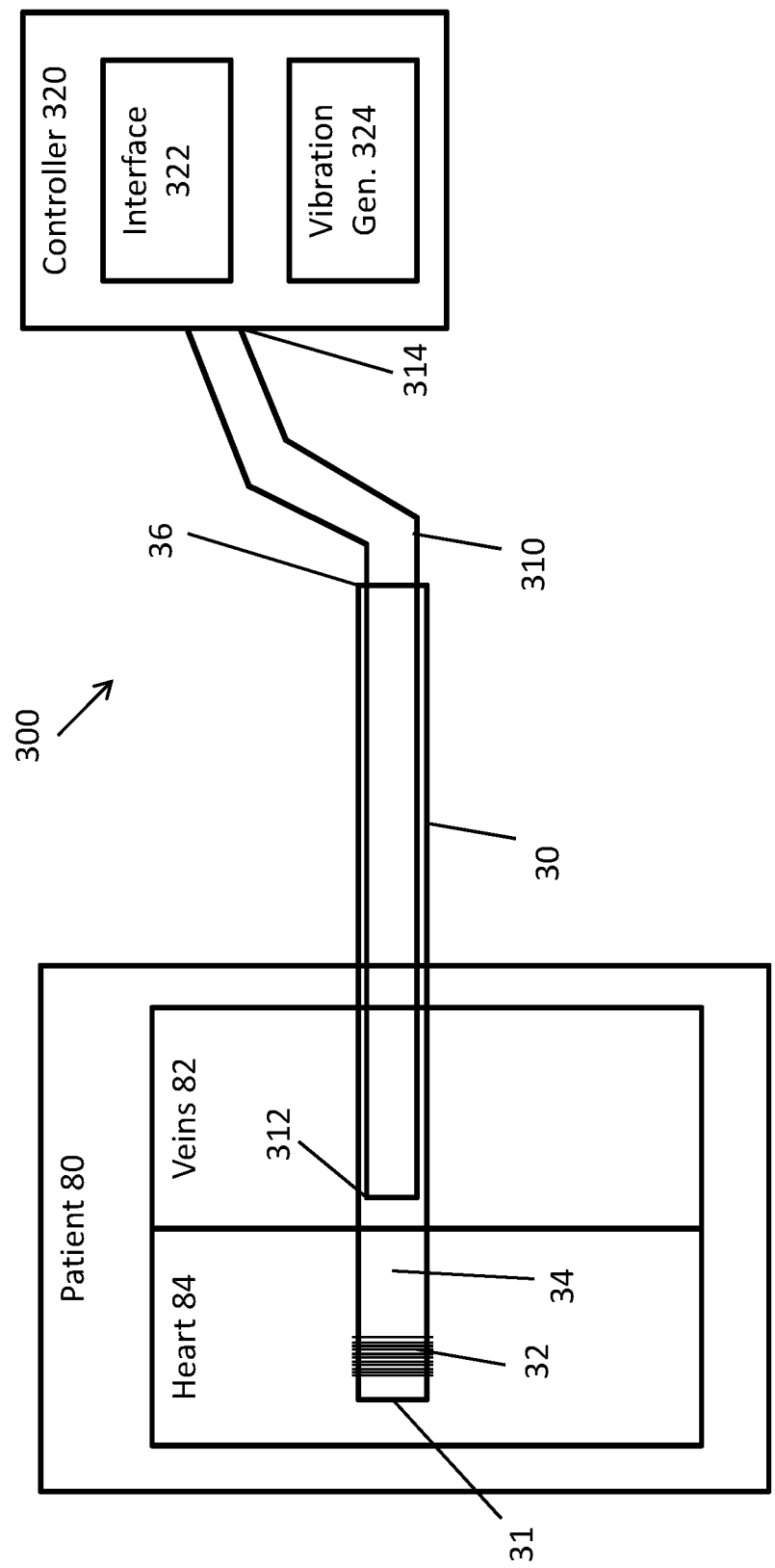
FIGS. 3A-3C are schematic system diagrams showing a system for lead removal according to some embodiments of the present disclosure.
Figure 3B:
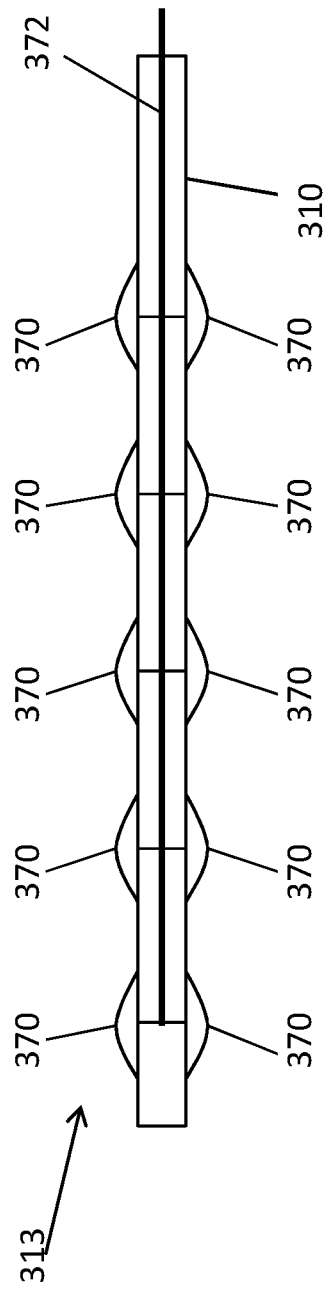
Figure 3C:
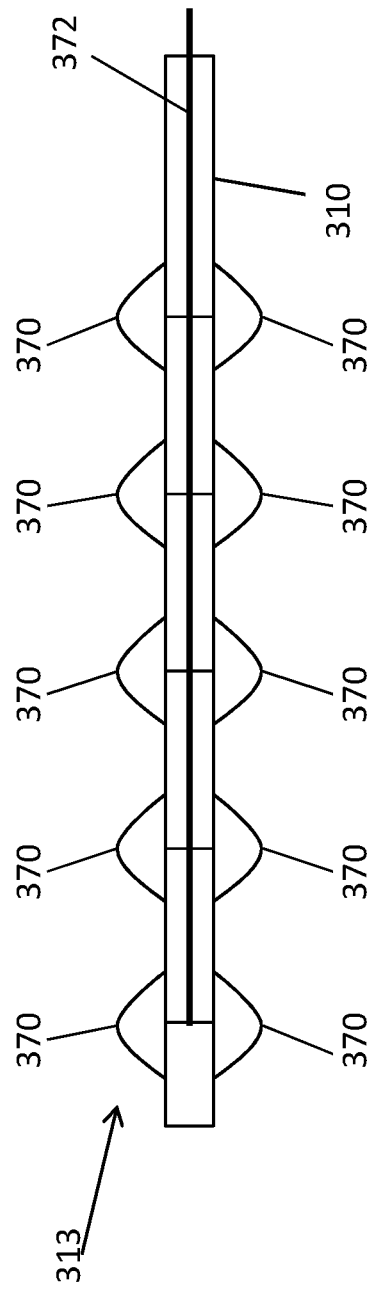

Reference is now made to FIGS. 3A-3C which are schematic system diagrams showing a system for lead removal according to some embodiments of the present disclosure. As shown in FIG. 3A a cardiac lead 30 has been implanted into a patient 80. The embodiment of FIGS. 3A-3C is the same as that shown in FIG. 1A, including components with the same numbering.

In the embodiment of FIGS. 3A-3C LRS 310 comprises locking mechanism 313 that extends along the entire length of LRS 310 that is to be inserted into lead 30. In the exemplary embodiment of FIGS. 3B-3C, locking mechanism 313 comprises multiple balloons 370 formed of an inflatable material positioned along the outer surface of LRS 310. Balloons 370 are inflated via inflating lumen 372. Inflating lumen 372 is connected on the proximal side of LRS 310 to an inflating device (not shown) and can optionally be manipulated by a medical practitioner to lock or unlock LRS 310 to lead 30 or alternatively can be manipulated by controller 120 to lock or unlock LRS 310 to lead 30. FIG. 3B shows locking mechanism 313 in an unlocked position (deflated) and FIG. 3C shows locking mechanism in a locked position when balloons 370 are inflated by a pressurized gas pumped into inflating lumen 372 to lock LRS 310 to the inner wall 39 of lead 30 along the entire length of insertion of LRS 310. When the gas is allowed to escape from balloons 370, balloons 372 deflate to unlock from inner wall 39 of lead 30. Although the locking mechanism 313 of FIGS. 3B-3C uses a balloon locking mechanism, it should be appreciated that any type of locking mechanism, including but not limited to the full-length variations of the locking mechanisms described in FIGS. 1C-1L are possible, implemented with multiple locking points, and the specific embodiment of FIGS. 1M-1N should not be considered limiting.

Figure 4A:
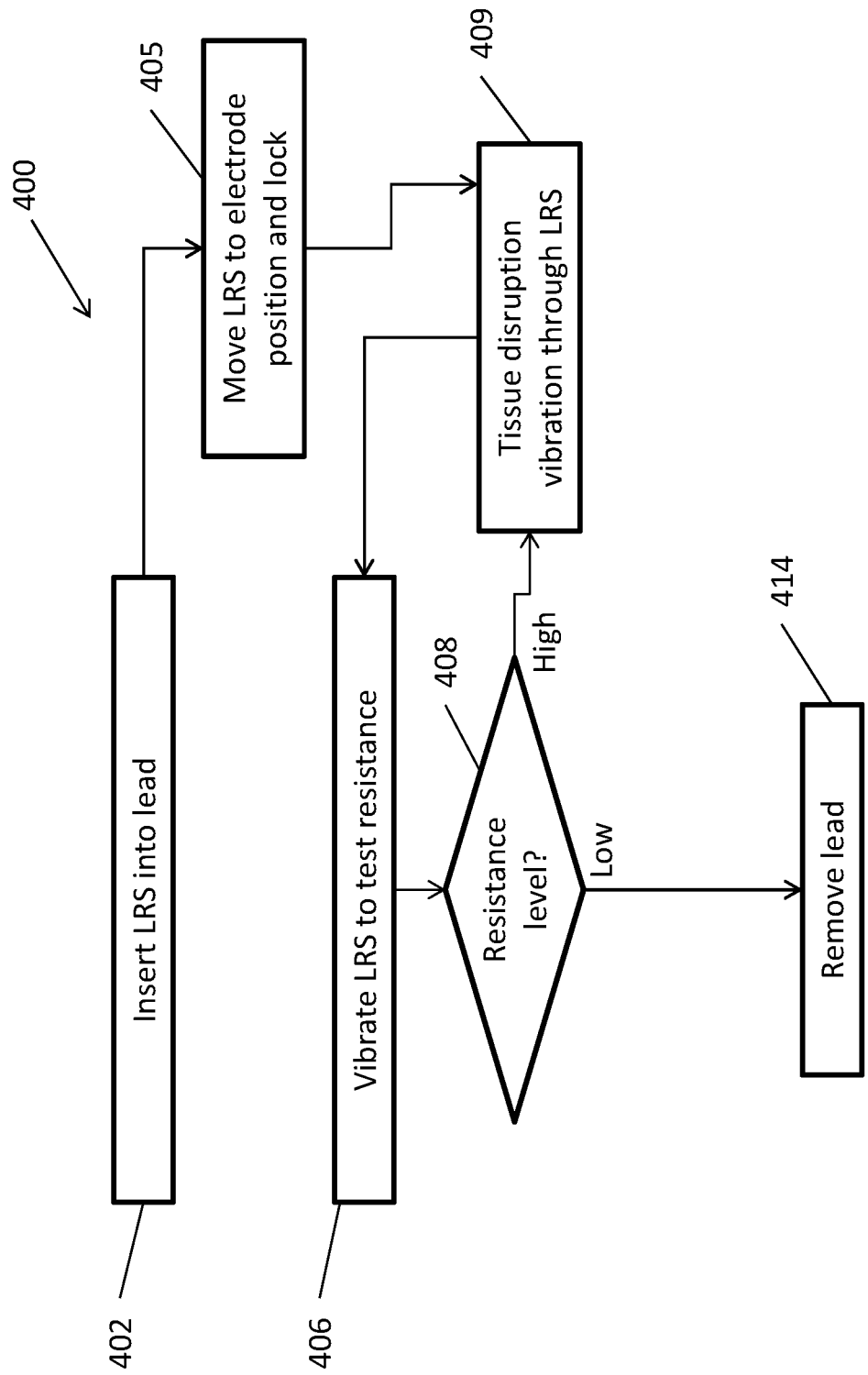
FIGS. 4A and 4B-4E are respectively a flow diagram and illustrative drawings showing a method of use of a lead removal stylet according to at least some embodiments of the present disclosure.
Figure 4B:
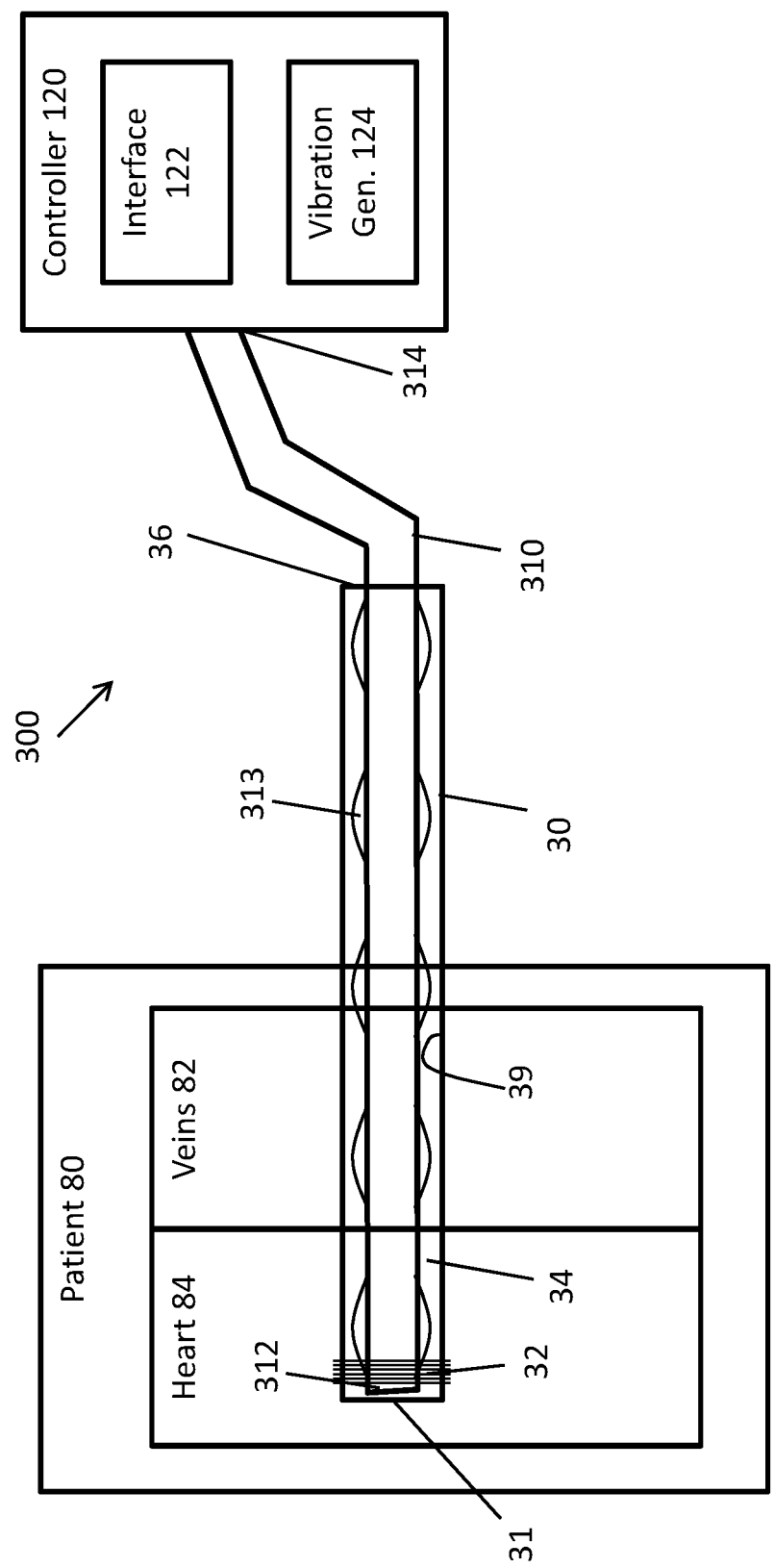

Reference is now made to FIGS. 4A and 4B-4E which are respectively a flow diagram and illustrative drawings showing a method of use of a lead removal stylet according to at least some embodiments of the present disclosure. In step 402 of process 400 as shown in FIG. 4B LRS 310 is inserted into the interior of lead 30. Steps 402, 405, 406, 408, and 409 are preferably automated and performed by controller 140 or alternatively by controller 140 along with a human operator.

Figure 4C:
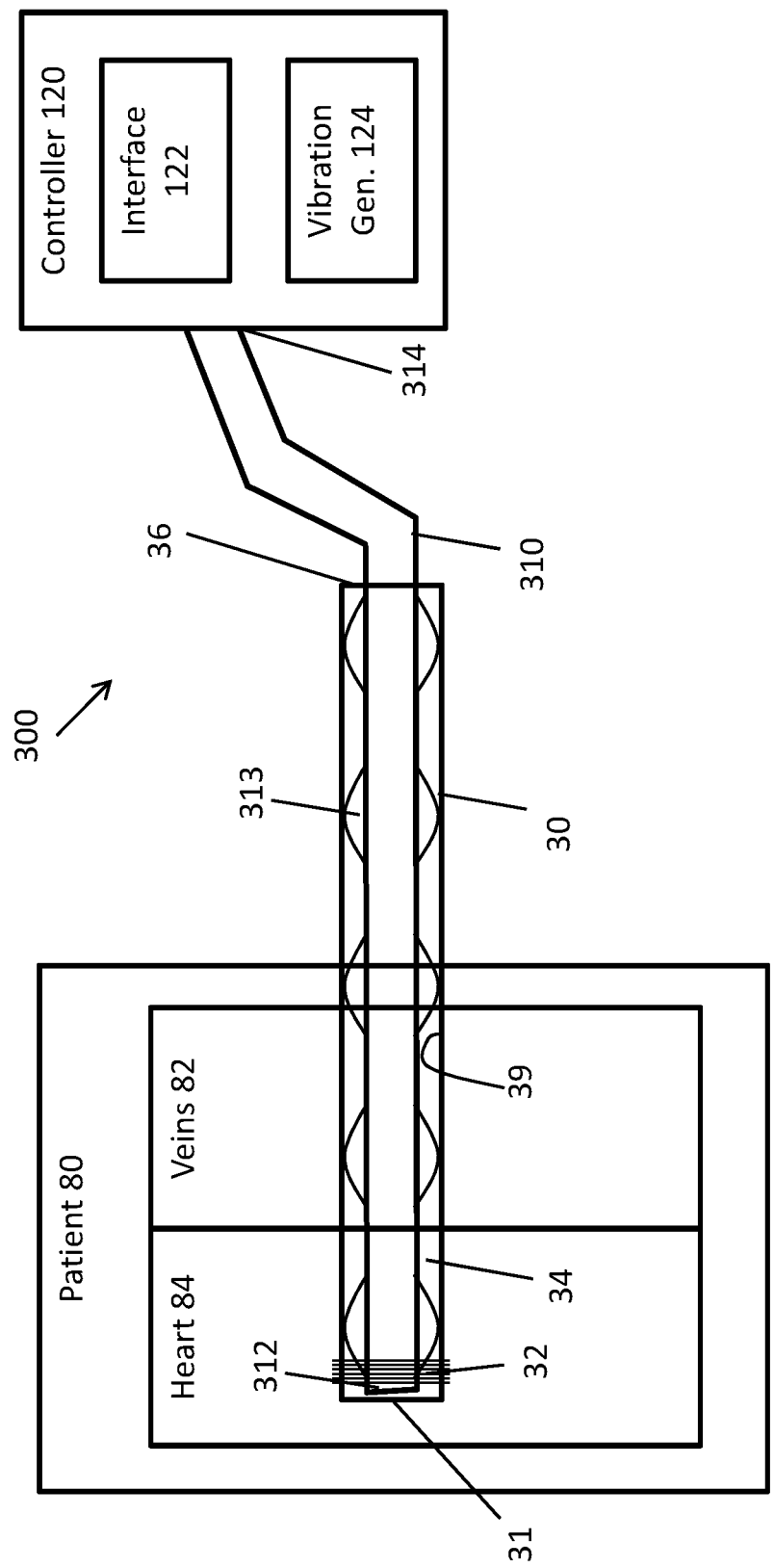

In step 405 and as in FIG. 4B, LRS 310 is moved to a starting position inside lead 30 and as in FIG. 4C; LRS 310 is locked against a plurality of points of the inner walls 39 of lead 30 by expanding locking mechanism 313. These positions are referred to herein as the locking positions. The starting locking position is preferably with LRS 310 pushed all the way into lead 30 such that the distal end 312 is adjacent to electrode 32.

Figure 4D:
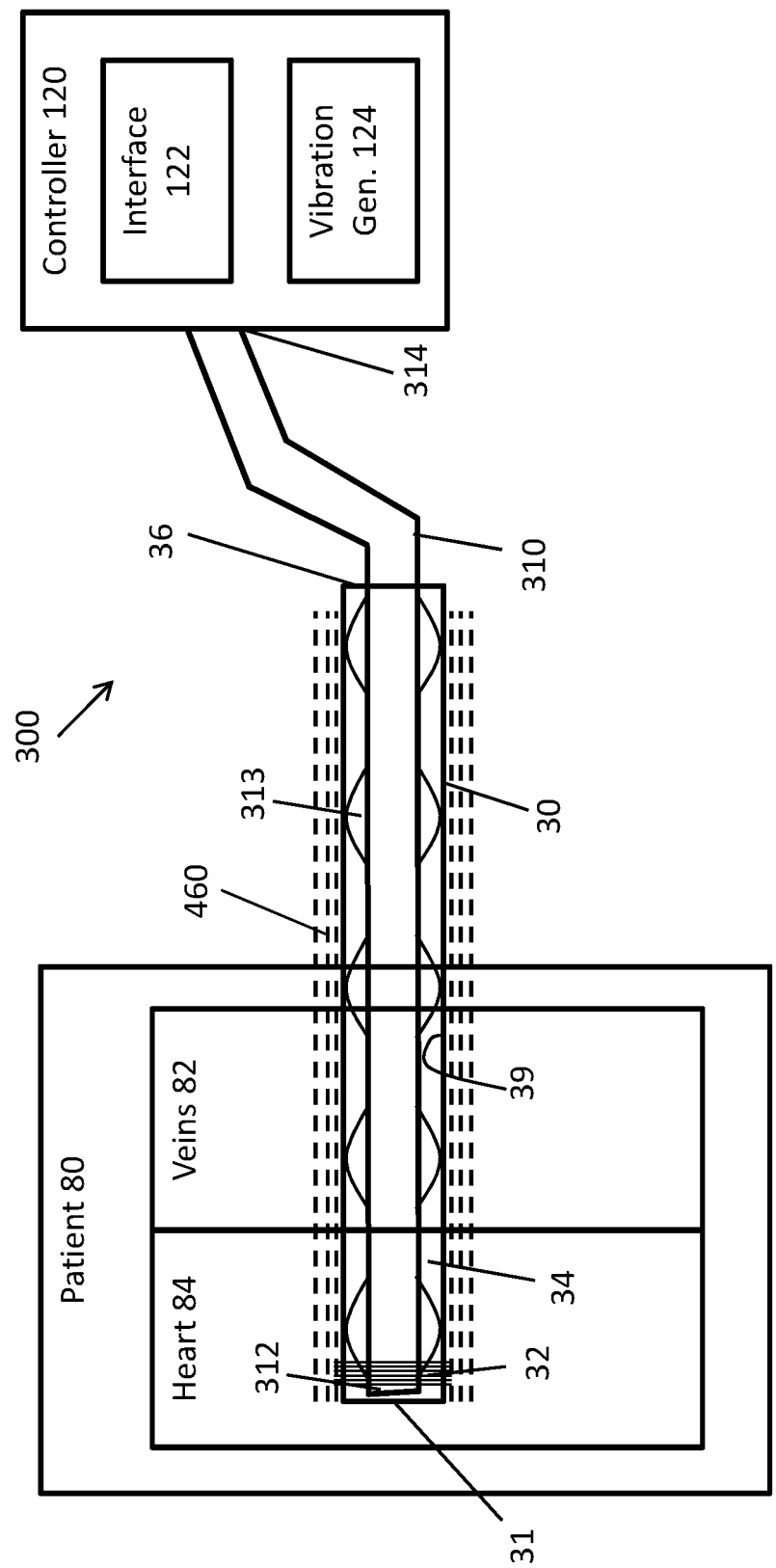

In step 409 LRS 310 is vibrated with a high amplitude tissue disrupting vibration 460 and as shown in FIG. 4D. The vibration is generated from controller generator 124 as in FIG. 3A. Tissue disrupting vibration 460 direction is horizontal, or vertical, or a combination of these. Vibration 460 direction, amplitude, period and frequency (collectively referred to as vibration type) are preferably predetermined based on experience with use of the system on a range of patients. Vibration 460 from LRS 310 is mechanically transferred to lead 30 at the plurality of locking positions where balloons 370 or other alternative locking mechanisms 313 lock against inner wall 39, and thus lead 30 also vibrates based on the selected vibration type. Vibration 460 ideally disrupts binding tissue holding lead 30.

Figure 4E:
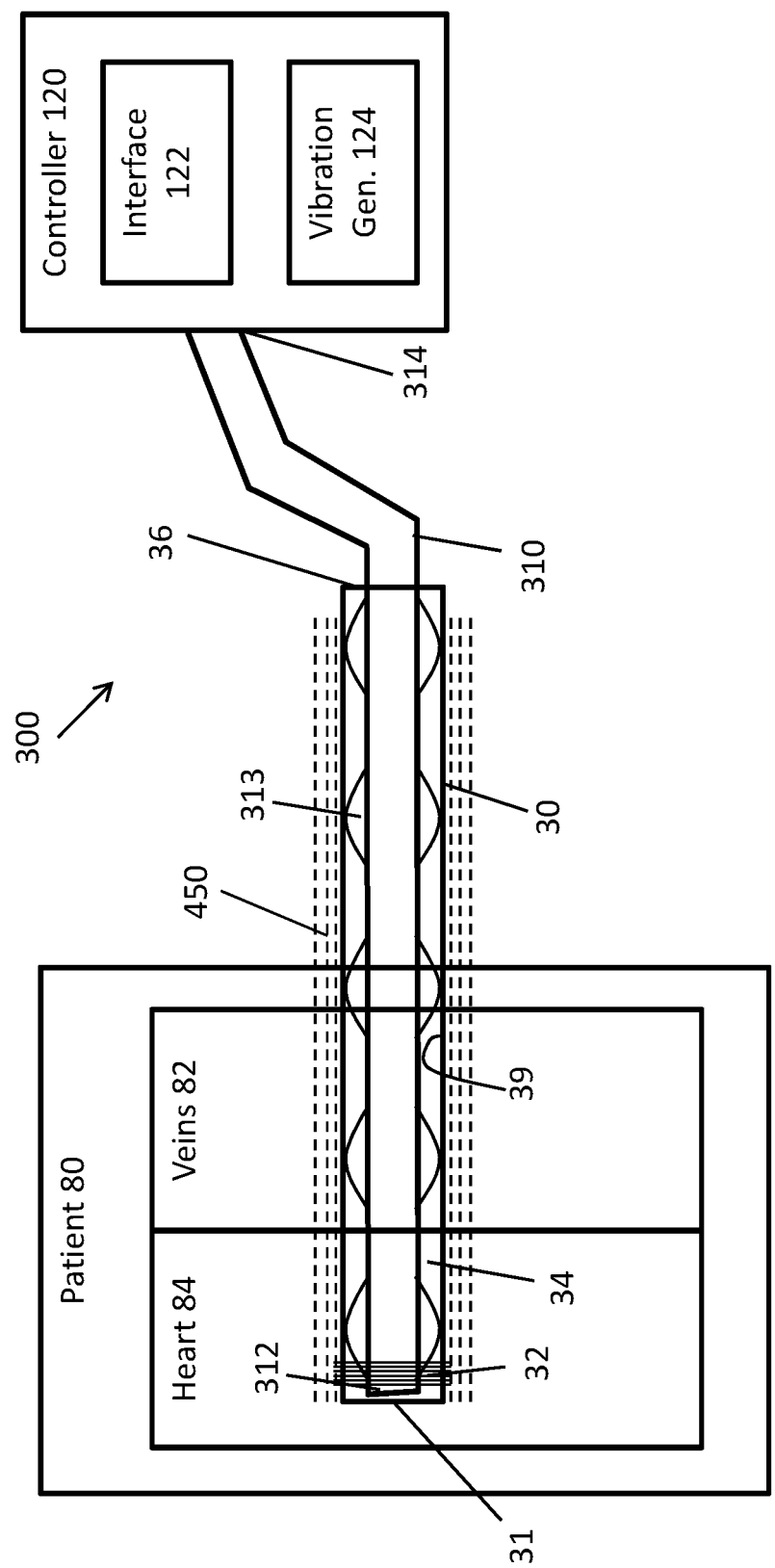

It must now be determined whether lead 30 is still held in place by binding tissue or not. Therefore in step 406 and as shown in FIG. 4E, low amplitude testing vibration 450 is activated in or applied to LRS 310 by controller 140 and the resistance to the vibration is measured by controller 140 in step 408. Depending on the measured resistance it is determined whether lead 30 is still held in place by binding tissue.

Test vibration 450 direction is horizontal, rotational, or vertical, or a combination of these in any or all planes. Vibration 450 direction, amplitude, period and frequency (collectively referred to as vibration type) are preferably predetermined based on experience with use of the system on a range of patients. Vibration 450 from LRS 310 is mechanically transferred to lead 30 at the plurality of locking positions where balloons 370 or other alternative locking mechanisms 313 lock against inner wall 39 and thus lead 30 also vibrates based on the selected vibration type but to varying degrees depending on the presence of binding tissue.

A high resistance to vibration in steps 406 and 408 indicates that lead 30 is stuck in binding tissue. In such cases, step 409 is repeated, and then steps 406 and 408 are repeated until a low resistance to vibration is detected. Subsequent reapplied tissue disrupting vibration 460 is optionally of a greater type with increase in one or more of period, frequency or amplitude and also optionally a different vibration direction. Optionally when a high resistance to vibration 450 is detected in steps 406 and 408, LRS 310 is unlocked, shifted forward or backward within lead 30, locked in position and step 409 is then repeated.

A low resistance to vibration 450 indicates that lead 30 is not stuck in binding tissue. Once it has been determined that resistance is lowered it is assumed that binding tissue has been disrupted and that lead 30 is now disconnected from binding tissue. Therefore in step 414 LRS 310 is now unlocked and lead 30 is removed by pulling it out of patient 80.

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

It is to be understood that the disclosure is not limited in its application to the details set forth in the description contained herein or illustrated in the drawings. The disclosure is capable of other embodiments and of being practiced and carried out in various ways. Those skilled in the art will readily appreciate that various modifications and changes can be applied to the embodiments of the disclosure as hereinbefore described without departing from its scope, defined in and by the appended claims.

The invention claimed is:

1. A method for extracting a lead from a patient comprising:
   a. providing a lead removal stylet (LRS);
   b. inserting said stylet into an interior of said lead;
   c. locking said stylet to a first locking position in the interior of said lead with a locking mechanism;
   d. vibrating said stylet with tissue disrupting vibration to cause said lead to vibrate and to perform a first disconnecting from binding tissue, wherein said locking mechanism transfers the vibrations from said stylet to said lead at the first locking position;
   e. moving said stylet and locking it to a second locking position in the interior of said lead with the locking mechanism; and
   f. vibrating said stylet with said tissue disrupting vibration to cause said lead to vibrate and to perform a second disconnecting from binding tissue, wherein said locking mechanism transfers the vibrations from said stylet to said lead at the second locking position.

2. The method of claim 1, further comprising vibrating said stylet with testing vibration to determine a resistance to said testing vibration.

3. The method of claim 2, wherein when said resistance to said testing vibration is high, said tissue disrupting vibration is applied.

4. The method of claim 3, further comprising determining the resistance to said testing vibration to determine whether further said tissue disruption vibration is required.

5. The method of claim 4, further comprising providing a controller for said lead removal stylet and wherein said locking said stylet in the interior of said lead, said vibrating said stylet with said tissue disrupting vibration, said vibrating said stylet with said testing vibration, and said determining the resistance to said testing vibration to determine whether further said tissue disruption vibration is required are all performed in the first locking position by said controller.

6. The method of claim 2, wherein said testing vibration has a lower amplitude than said tissue disrupting vibration.

7. The method of claim 1, further comprising removing said lead.

8. The method of claim 1, wherein the first locking position for locking said stylet in the interior of said lead is adjacent to said binding tissue.

9. The method of claim 1, wherein the stylet is locked in the first locking position in the interior of the lead along a full length of the lead.

10. A method for extracting a lead from a patient comprising:

a. providing a lead removal stylet;
b. inserting said stylet into an interior of said lead;
c. locking said stylet to a first locking position in the interior of said lead with a locking mechanism;
d. providing a controller for said lead removal stylet and attaching a proximal end of the stylet to said controller for allowing said stylet to vibrate with tissue disrupting vibration;
e. vibrating said stylet with a first testing vibration to determine a resistance to said first testing vibration at the first locking position, wherein when said resistance to said first testing vibration is high, the method further comprises causing said lead to vibrate and to perform a first disconnecting from binding tissue, wherein said locking mechanism transfers the vibrations from said stylet to said lead at the first locking position;
f. moving said stylet and locking it to a second locking position in the interior of said lead with the locking mechanism; and
g. vibrating said stylet with a second testing vibration to determine a resistance to said second testing vibration at the second locking position, wherein when said resistance to said second testing vibration is high, the method further comprises causing said lead to vibrate and to perform a second disconnecting from binding tissue, wherein said locking mechanism transfers the vibrations from said stylet to said lead at the second locking position.

* * * * *